United States Patent [19]
Kato et al.

[11] Patent Number: 6,083,370
[45] Date of Patent: Jul. 4, 2000

[54] GAS SENSOR

[75] Inventors: Nobuhide Kato, Ama-gun; Yasuhiko Hamada, Nagoya, both of Japan

[73] Assignee: NGK Insulators, Ltd., Japan

[21] Appl. No.: 08/985,703

[22] Filed: Dec. 5, 1997

[30] Foreign Application Priority Data

Dec. 20, 1996 [JP] Japan ................................. 8-341926
Oct. 7, 1997 [JP] Japan ................................. 9-274218

[51] Int. Cl.$^7$ ................................. G01N 27/407
[52] U.S. Cl. .................. 204/425; 204/426; 204/427; 205/781; 205/784; 205/786.5; 205/788
[58] Field of Search ................... 204/421–429; 205/783.5, 784, 784.5, 785, 781, 786.5, 788

[56] References Cited

U.S. PATENT DOCUMENTS

| | | | |
|---|---|---|---|
| 4,167,163 | 9/1979 | Moder | 204/424 |
| 4,505,805 | 3/1985 | Mase et al. | 204/425 |
| 4,543,176 | 9/1985 | Harada et al. | 204/425 |
| 4,609,453 | 9/1986 | Shimomura | 204/426 |
| 5,547,552 | 8/1996 | Hasegawa et al. | 204/401 |
| 5,672,811 | 9/1997 | Kato et al. | 204/426 |
| 5,709,198 | 1/1998 | Sagisaka et al. | 204/401 |
| 5,763,763 | 6/1998 | Kato et al. | 204/429 |

FOREIGN PATENT DOCUMENTS

| | | |
|---|---|---|
| 58-178248 | 10/1983 | Japan . |
| 63-38154 | 2/1988 | Japan . |
| 64-39545 | 2/1989 | Japan . |
| 1-277751 | 11/1989 | Japan . |
| 2-1543 | 1/1990 | Japan . |
| 7-45004 | 10/1995 | Japan . |

OTHER PUBLICATIONS

Patent Abstracts of Japan, vol. 10, No. 324 (P–512), Nov. 5, 1986 & JP 61 132851 A (Nippon Denso Co) *abstract*.
Patent Abstracts of Japan, vol. 8, No. 18 (P–250), Jan. 16, 1984 & JP 58 178248 A (Toyota), Oct. 19, 1983, *abstract*.

*Primary Examiner*—T. Tung
*Attorney, Agent, or Firm*—Parkhurst & Wendel, L.L.P.

[57] ABSTRACT

Disclosed is a gas sensor comprising a main pumping cell for pumping-processing oxygen contained in a measurement gas introduced into a first chamber, an auxiliary pumping cell for pumping-processing oxygen contained in the measurement gas introduced into a second chamber, a measuring pumping cell for pumping-processing oxygen in the measurement gas introduced via a third diffusion rate-determining section, an ammeter for detecting a pumping current generated depending on an amount of oxygen pumping-processed by the measuring pumping cell, a heater for heating at least the main pumping cell, the auxiliary pumping cell, and the measuring pumping cell to a predetermined temperature, an impedance-detecting circuit for detecting an impedance between an inner pumping electrode and an auxiliary pumping electrode, and a heater control circuit for controlling electric power application to the heater on the basis of a value of the impedance detected by the impedance-detecting circuit. Accordingly, it is possible to realize suppression of variation in detection output which would be otherwise caused depending on the measurement gas temperature and a high S/N ratio of detection output.

18 Claims, 15 Drawing Sheets

F I G. 5
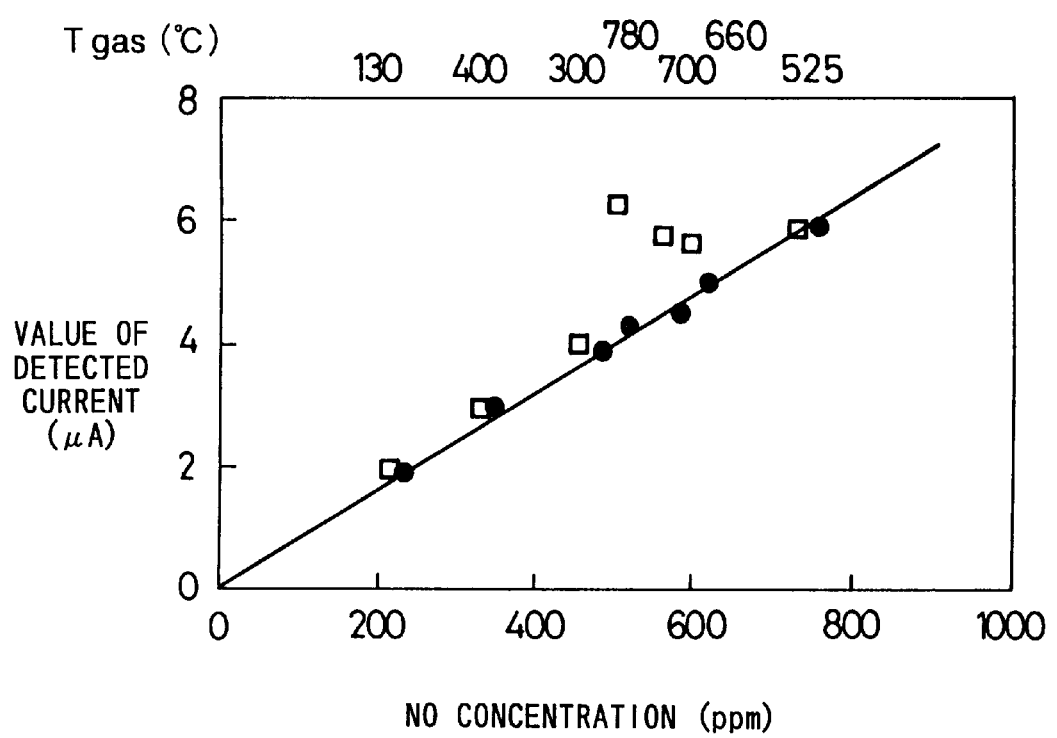

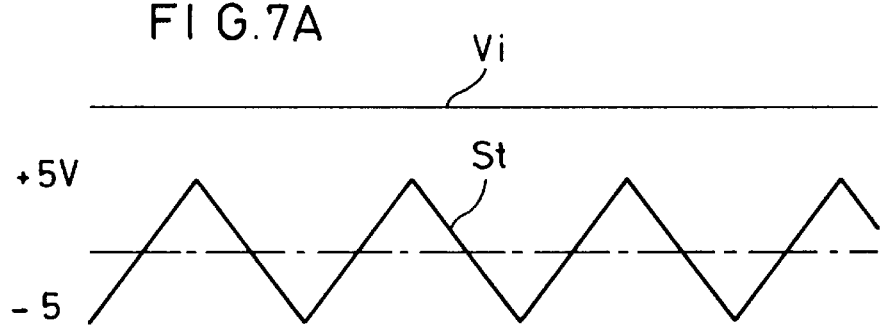
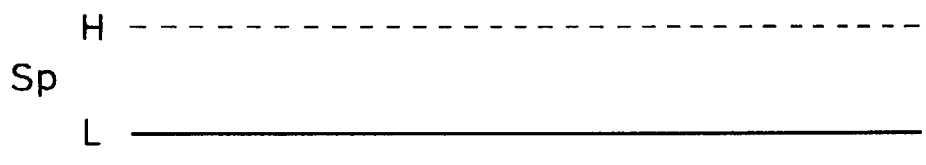
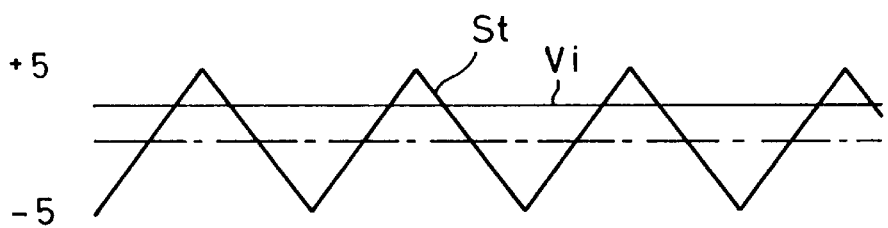
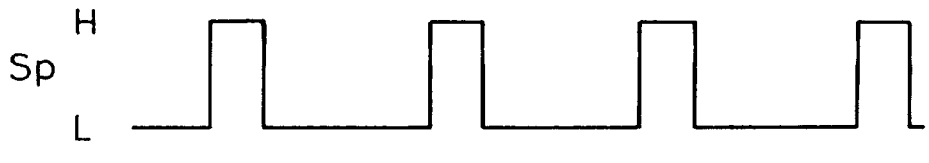

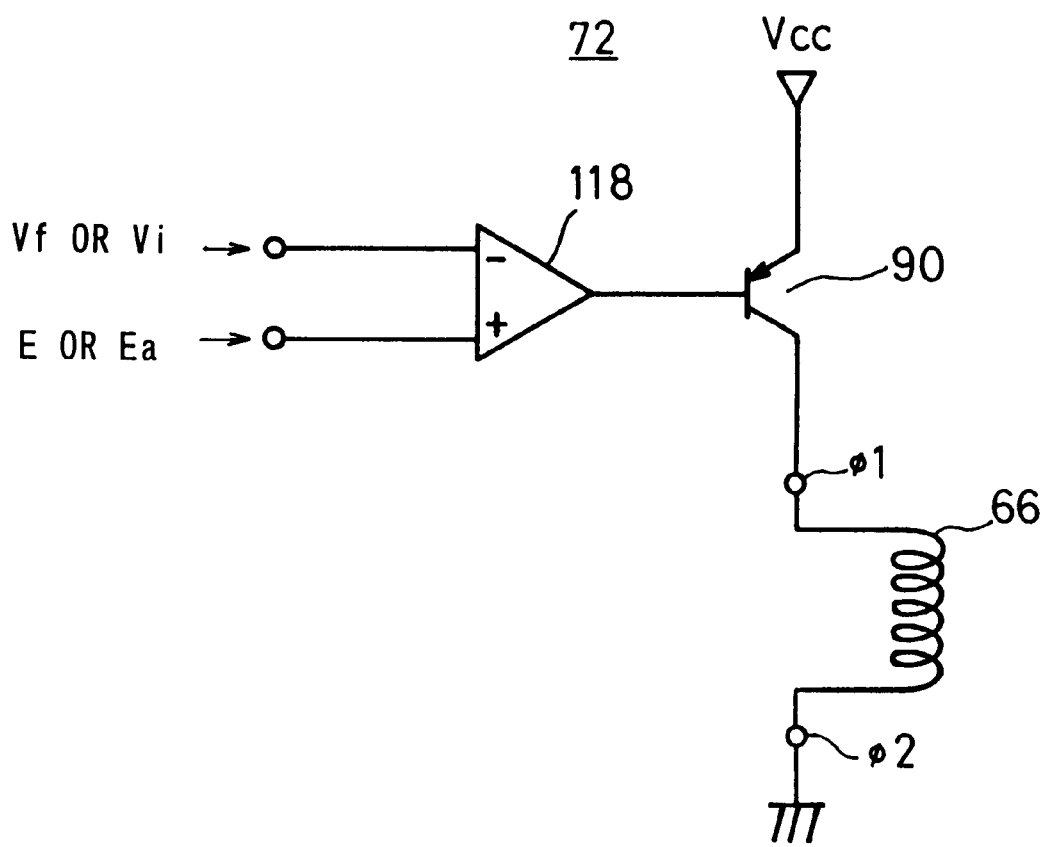

F I G. 14
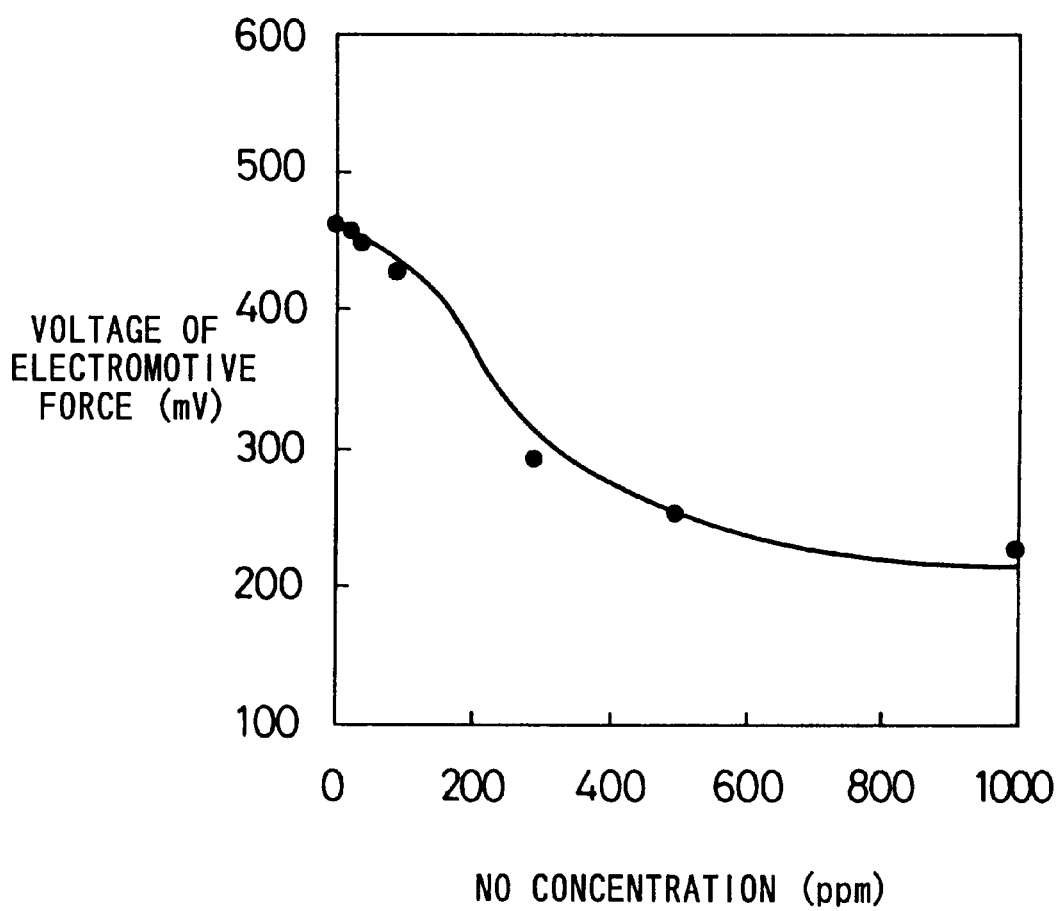

GAS SENSOR

BACKGROUND OF THE INVENTION

1. Field of the Invention

The present invention relates to a gas sensor for measuring oxides such as NO, $NO_2$, $SO_2$, $CO_2$, and $H_2O$ contained in, for example, atmospheric air and exhaust gas discharged from vehicles or automobiles, and inflammable gases such as CO and CnHm.

2. Description of the Related Art

Various measuring systems and apparatuses have been hitherto suggested in order to know the concentration of a predetermined gas component in a measurement gas.

For example, those known as the method for measuring NOx in a measurement gas such as combustion gas include a technique in which the NOx-reducing ability of Rh is utilized while using a sensor comprising a Pt electrode and an Rh electrode formed on an oxygen ion-conductive solid electrolyte such as zirconia to measure an electromotive force generated between the both electrodes.

The sensor as described above suffers the following problem. That is, the electromotive force is greatly changed depending on the change in concentration of oxygen contained in a combustion gas as a measurement gas. Moreover, the change in electromotive force is small with respect to the change in concentration of NOx. For this reason, the conventional sensor tends to suffer influence of noise. Further, in order to bring out the NOx-reducing ability, it is indispensable to use a reducing gas such as CO. For this reason, the amount of produced CO is generally smaller than the amount of produced NOx under a lean fuel combustion condition in which a large amount of NOx is produced. Therefore, the conventional sensor has a drawback in that it is impossible to perform measurement for a combustion gas produced under such a combustion condition.

A system has been disclosed, for example, in Japanese Laid-Open Patent Publication Nos. 63-38154 and 64-39545, in which a pair of electrochemical pumping cell and sensor cell comprising Pt electrode and an oxygen ion-conductive solid electrolyte are combined with another pair of electrochemical pumping cell and sensor cell comprising Rh electrode and an oxygen ion-conductive solid electrolyte to measure NOx in accordance with a difference between respective pumping current values.

Further, for example, Japanese Laid-Open Patent Publication Nos. 1-277751 and 2-1543 disclose the following method. That is, two pairs of electrochemical pumping cells and sensor cells are prepared. The limiting pumping current is measured at a partial pressure of oxygen at which NOx is not reduced, by using a sensor comprising one of the pairs of pumping cells and sensor cells, while the limiting pumping current is measured at a partial pressure of oxygen at which NOx is reduced, by using a sensor comprising the other pair of pumping cell and sensor cell so that the difference between the limiting pumping currents is determined. Besides, the difference in limiting current is measured by using a sensor comprising a pair of pumping cell and sensor cell, while switching the partial pressure of oxygen in a measurement gas between a partial pressure of oxygen at which NOx is reduced and a partial pressure of oxygen at which NOx is not reduced.

In principle, the output value obtained from the gas sensor as described above involves strong dependency on temperature, and hence it is necessary to perform temperature compensation. The temperature of the gas sensor is correlated with the alternating current resistance (impedance) of the gas sensor. Specifically, the impedance of the gas sensor is lowered as the temperature of the gas sensor is raised.

A constant resistance control method based on the use of a bridge has been hitherto employed as a technique for performing temperature compensation for the gas sensor. According to the constant resistance control method, the total resistance of a heater (=resistance of heat-generating section of heater+resistance of heater lead section) is controlled on the basis of the temperature of a measurement gas.

As described above, the total resistance of the heater is controlled in the constant resistance control method. Accordingly, when the resistance value of the heater lead section contained in the element is increased in accordance with the increase in measurement gas temperature, the control is made so that the resistance value of the heat-generating section of the heater is decreased. As a result, a phenomenon occurs in which the output of the heater is lowered.

Such a system involves the following inconvenience. That is, the temperature at a portion for sensing the predetermined gas component may be deviated from a predetermined designed value. As a result, a phenomenon occurs in the output characteristic of the gas sensor, in which the detection current value is shifted with respect to the concentration of the predetermined gas component. Specifically, the detection current value is increased, as the temperature is raised, as compared with a prescribed detection current value which is expected based on the concentration of the predetermined gas component, and thus the detection accuracy is deteriorated.

In order to dissolve the foregoing inconvenience, it is necessary to decrease the resistance value of the heater lead section as small as possible, resulting in a problem that the degree of freedom is lowered concerning wiring arrangement design.

A gas sensor has been hitherto suggested, as an alternative of the constant resistance control method described above, which comprises a means for measuring an impedance of the gas sensor, and a current control unit for controlling electric power application to a heater so that the impedance of the gas sensor is constant (see, for example, Japanese Laid-Open Patent Publication No. 58-178248). In the gas sensor described above, an amount of alternating current is superimposed on an electric power source, while a circuit is provided for detecting the impedance generated in accordance therewith. Thus, the current to be supplied to the heater is controlled so that the impedance is constant.

Further, a gas sensor has been also hitherto suggested, in which only a direct current component is positively feedback-controlled in order to avoid oscillation in a current control system (feedback control system) for a heater on the basis of a detected impedance (see, for example, Japanese Utility Model Publication No. 7-45004).

However, in the case of the gas sensor including the conventional heater current control system, the alternating current flows to the detecting electrode which is used to detect the predetermined gas component. For this reason, the alternating current appears as a noise, and it is feared that the S/N ratio of the detection output is deteriorated.

SUMMARY OF THE INVENTION

The present invention has been made taking the foregoing problems into consideration, an object of which is to provide a gas sensor which makes it possible to suppress variation in detection output brought about depending on the temperature of a measurement gas, and which makes it possible to realize a high S/N ratio of the detection output.

Another object of the present invention is to provide a gas sensor which makes it possible, in addition to the foregoing requirement, to monitor a temperature on a side of a main pumping means and a temperature on a side of a measuring pumping means (or a concentration-detecting means) in a sensor element, and which makes it possible to highly accurately control the temperature in the sensor element.

Still another object of the present invention is to provide a gas sensor which makes it possible, in addition to the foregoing requirement, to constantly and highly accurately control the temperature in a sensor element, especially the temperature in the vicinity of a detecting electrode, and which makes it possible to further suppress output variation in detection output.

Still another object of the present invention is to provide a gas sensor which makes it possible, in addition to the foregoing requirement, to achieve a simplified control circuit system.

According to the present invention, there is provided a gas sensor comprising:

a main pumping means including a solid electrolyte contacting with an external space, and an inner pumping electrode and an outer pumping electrode formed on inner and outer surfaces of the solid electrolyte, for pumping-processing (pumping in and pumping out) a predetermined gas component contained in a measurement gas introduced from the external space, on the basis of a control voltage applied between the electrodes;

a measuring pumping means including a solid electrolyte and a detecting electrode and a reference electrode formed on the solid electrolyte, for pumping-processing the predetermined gas component contained in the measurement gas after being pumping-processed by the main pumping means, on the basis of a voltage applied between the detecting electrode and the reference electrode;

a current-detecting means for detecting a pumping current generated depending on an amount of the predetermined gas component pumping-processed by the measuring pumping means;

a heater for heating at least the main pumping means and the measuring pumping means to a predetermined temperature;

an impedance-detecting means for detecting an impedance between an electrode disposed on a side of the main pumping means and an electrode disposed on a side of the measuring pumping means; and a heater control means for controlling electric power application to the heater on the basis of a value of the impedance detected by the impedance-detecting means.

The electrode disposed on the side of the main pumping means includes the electrodes for constructing the main pumping means as well as the electrodes disposed in the vicinity of the main pumping means. The electrode disposed on the side of the electric signal-generating conversion means includes the electrodes for constructing the electric signal-generating conversion means as well as the electrodes disposed in the vicinity of the electric signal-generating conversion means.

According to the present invention, at first, the predetermined gas component contained in the measurement gas introduced from the external space is subjected to pumping processing effected by the main pumping means. Thus, the predetermined gas component is adjusted to have a predetermined concentration.

The measurement gas, which has been adjusted for the concentration of oxygen by the main pumping means, is introduced into the electric signal-generating conversion means in the next step. The electric signal-generating conversion means generates, by conversion, an electric signal corresponding to the amount of the predetermined gas component contained in the measurement gas after being pumping processed by the main pumping means. The amount of the specified component in the measurement gas is measured on the basis of the electric signal supplied from the electric signal-generating conversion means.

When the electric signal-generating conversion means is constructed by the measuring pumping means and the current-detecting means, the measurement gas, which has been adjusted for the oxygen concentration by the main pumping means, is introduced into the measuring pumping means.

The measuring pumping means pumping-processes the predetermined gas component of the measurement gas, on the basis of the voltage applied between the detecting electrode and the reference electrode. The pumping current, which is generated in the measuring pumping means corresponding to the amount of the predetermined gas component pumping-processed by the measuring pumping means, is detected by the current-detecting means. The amount of the specified component in the measurement gas is determined on the basis of an obtained detected value.

Alternatively, when the electric signal-generating conversion means comprises a concentration-detecting means and a voltage-detecting means, the measurement gas, which has been adjusted for the oxygen concentration by the main pumping means, is introduced into the concentration-detecting means in the next step. The concentration-detecting means generates an electromotive force corresponding to a difference between an amount of the predetermined gas component contained in the measurement gas after being pumping-processed by the main pumping means and an amount of the predetermined gas component existing in the reference gas on the side of the reference electrode.

The electromotive force is detected by the voltage-detecting means disposed at the downstream stage, and the amount of the specified component in the measurement gas is determined on the basis of an obtained detected value.

The detecting operation as described above is performed while heating at least the main pumping means and the measuring pumping means, as well as the main pumping means and the concentration-detecting means by means of the heater. Accordingly, the amount of the predetermined gas component is highly accurately detected (concerning detection of the pumping current and generation of the electromotive force) by the measuring pumping means and the concentration-detecting means.

During the period in which the foregoing operation is performed, the impedance value between the electrode disposed on the side of the main pumping means and the electrode disposed on the side of the electric signal-generating conversion means (the measuring pumping means or the concentration-detecting means) is detected by the aid of the impedance-detecting means. The electric power application to the heater is controlled on the basis of the detected impedance value by the aid of the heater control means.

Specifically, when the temperature of the measurement gas is raised over a predetermined temperature, and the impedance value is decreased, then the control is made such that the amount of electric power application to the heater is decreased, or the electric power application to the heater is stopped. Accordingly, the temperature in the sensor element is gradually lowered.

On the contrary, when the temperature of the measurement gas is lowered under a predetermined temperature, and the impedance value is increased, then the control is made such that the amount of electric power application to the heater is increased, or the electric power application to the heater is started. Accordingly, the temperature in the sensor element is gradually raised. Thus, the temperature in the sensor element can be maintained to be constant by controlling the electric power application to the heater on the basis of the impedance value.

Therefore, when the present invention is compared with the conventional constant resistance control method, it is unnecessary to manufacture a gas sensor having a strict resistance ratio between the resistance value of the heater lead section and the resistance value of the heat-generating section of the heater. Moreover, it is possible to avoid the influence of the temperature of the measurement gas, which would be otherwise exerted due to the increase in resistance value of the heater lead section. Especially, in the present invention, the impedance value between the electrode disposed on the side of the main pumping means and the electrode disposed on the side of the electric signal-generating conversion means (the measuring pumping means or the concentration-detecting means) is detected. Accordingly, it is possible to monitor the temperature on the side of the main pumping means and the temperature on the side of the electric signal-generating conversion means in the sensor element. Therefore, it is possible to highly accurately control the temperature in the sensor element.

In the gas sensor constructed as described above, it is preferable that the electrode disposed on the side of the electric signal-generating conversion means, which is subjected to the detection of the impedance performed by the impedance-detection means, is an electrode except for the detecting electrode.

In this embodiment, when the measuring pumping means is used as the electric signal-generating conversion means, the voltage applied to the measuring pumping means is free from variation caused by the detection of the impedance. Accordingly, it is possible to suppress, for example, superimposition of noise and fluctuation of the pumping current detected by the current-detecting means.

When the concentration-detecting means is used as the electric signal-generating conversion means, the electromotive force generated in the concentration-detecting means is free from variation caused by the detection of the impedance. Accordingly, it is possible to suppress, for example, superimposition of noise and fluctuation of the electromotive force (voltage) detected by the voltage-detecting means.

In other words, in the gas sensor according to the present invention, it is possible to suppress variation in detection output which would be otherwise caused depending on the temperature of the measurement gas, and it is possible to realize a high S/N ratio of the detection output.

Preferably, the gas sensor according to the present invention may further comprises a concentration-measuring means for generating an electromotive force corresponding to a difference between an amount of the predetermined gas component contained in the measurement gas during the pumping process performed by the main pumping means and an amount of the predetermined gas component contained in a reference gas existing on a side of the reference electrode; and a main pumping control means for adjusting a level of the control voltage applied between the inner pumping electrode and the outer pumping electrode, on the basis of a voltage of the electromotive force.

Accordingly, the concentration-measuring means generates the electromotive force corresponding to the difference between the amount of the predetermined gas component contained in the measurement gas during the pumping process performed by the main pumping means and the amount of the predetermined gas component contained in the reference gas existing on the side of the reference electrode. The level of the control voltage applied between the inner pumping electrode and the outer pumping electrode of the main pumping means is adjusted on the basis of the electromotive force by the aid of the main pumping control means.

The main pumping means pumping-processes the predetermined gas component contained in the measurement gas introduced from the external space, in an amount corresponding to the level of the control voltage. When the level-adjusted control voltage is supplied to the main pumping means, the concentration of the predetermined gas component contained in the measurement gas is subjected to feedback control to achieve the predetermined level.

In the present invention, the electromotive force generated by the concentration-measuring means is a terminal voltage generated at least between the reference electrode and the measuring electrode formed in the vicinity of the main pumping means. Alternatively, the electromotive force is a terminal voltage generated at least between the reference electrode and the inner pumping electrode of the main pumping means.

Especially, in the invention in which the terminal voltage between the reference electrode and the inner pumping electrode is measured by using the concentration-measuring means, when the pumping amount of the predetermined gas component effected by the main pumping means, and the concentration of the predetermined gas component in the measurement gas is changed, then the terminal voltage between the reference electrode and the inner pumping electrode of the main pumping means is changed without any time delay. Accordingly, no oscillation phenomenon occurs in the feedback control.

In the invention described above, it is also preferable that the impedance-detecting means comprises an alternating current-generating circuit for supplying an alternating current between the electrodes subjected to the detection, and a signal-detecting circuit for detecting a voltage signal at a level corresponding to the impedance between the electrodes generated between the electrodes by supplying the alternating current between the electrodes subjected to the detection; and the heater control means comprises a comparator circuit for comparing a reference level with the level of the voltage signal supplied from the signal-detecting circuit of the impedance-detecting means, and a switching circuit for performing ON/OFF control over electric power application to the heater on the basis of a result of comparison performed by the comparator circuit.

Accordingly, at first, the alternating current is supplied between the electrodes subjected to the detection, by the aid of the alternating current-generating circuit of the impedance-detecting means. The voltage signal at the level corresponding to the impedance between the electrodes is generated between the electrodes by supplying the alternating current. The voltage signal is detected by the signal-detecting circuit. The voltage signal detected by the signal-detecting circuit is supplied to the heater control means disposed at the downstream stage. In the heater control means, at first, the comparator circuit is used to compare the level of the supplied voltage signal with the reference level. The result of comparison obtained by the comparator circuit is supplied to the switching circuit disposed at the downstream stage. The switching circuit controls electric power application to the heater on the basis of the supplied result of comparison.

Specifically, when the impedance between the electrodes except for the detecting electrode is lowered in accordance with the increase in temperature of the measurement gas, and the result of comparison indicates, for example, the fact that "the level of the voltage signal is lower than the reference level", then the switching circuit stops electric power application to the heater. Accordingly, the temperature in the sensor element is gradually lowered.

On the contrary, when the impedance between the electrodes is increased in accordance with the decrease in temperature of the measurement gas, and the result of comparison indicates, for example, the fact that "the level of the voltage signal is higher than the reference level", then the switching circuit starts electric power application to the heater. Accordingly, the temperature in the sensor element is gradually raised.

The temperature in the sensor element is quickly converged to a constant temperature owing to the operation performed as described above.

It is preferable for the gas sensor constructed as described above that the signal-detecting circuit is provided with a filter circuit for converting the alternating current signal generated between the electrodes into the voltage signal at the level corresponding to the impedance between the electrodes. For example, a low-pass filter and a band-pass filter may be used as the filter circuit.

It is preferable for the gas sensor constructed as described above that the alternating current-generating circuit is wired and connected such that the alternating current is supplied not only between the electrodes but also to a resistor designed to have a resistance value corresponding to a normal impedance between the electrodes, and that the signal-detecting circuit comprises a first detection circuit for converting the alternating current generated between the electrodes into a voltage signal at a level corresponding to the impedance between the electrodes, a second detection circuit for converting an alternating current signal generated in the resistor into a voltage signal at a level corresponding to an impedance of the resistor, to be used as a reference signal, and a differential circuit for determining a difference between the voltage signal outputted from the first detection circuit and the reference signal outputted from the second detection circuit, and outputting the difference as a deviation signal.

Accordingly, at first, the alternating current is supplied between the electrodes except for the detecting electrodes by the aid of the alternating current-generating means of the impedance-detecting means, simultaneously with which the alternating current is also supplied to the resistor set to have the resistance value corresponding to the normal impedance between the electrodes.

The supply of the alternating current between the electrodes allows the alternating current signal generated between the electrodes to be supplied to the first detection circuit, and the signal is converted, for example, into a direct current voltage signal at the level corresponding to the impedance between the electrodes. On the other hand, the supply of the alternating current to the resistor allows the alternating current generated in the resistor to be supplied to the second detection circuit, and the signal is converted, for example, into a direct current voltage signal (reference signal) at the level corresponding to the impedance of the resistor.

Both of the voltage signal outputted from the first detection circuit and the reference signal outputted from the second detection circuit are supplied to the differential circuit. The differential circuit determines the difference between the voltage signal and the reference signal, and the obtained result is outputted as the deviation signal.

The deviation signal outputted from the differential circuit, especially its deviation level, is compared with the reference level by the comparator circuit of the heater control means disposed at the downstream stage. If the deviation level is, for example, lower than the reference level, for example, electric power application to the heater is stopped. On the contrary, if the deviation level is, for example, higher than the reference level, electric power application to the heater is started.

In the present invention, the target impedance value is set by using the resistor (pure resistance). Accordingly, it is unnecessary to use, as the first and second detection circuits for converting the alternating current signal into the voltage signal, a circuit device having a complicated circuit system such as a higher-order low-pass filter and a band-pass filter based on the use of an operational amplifier. The system of the present invention can be realized by using a simple rectifying circuit based on the use of a first-order low-pass filter and a diode. Thus, it is possible to effectively achieve simplification of the circuit arrangement and reduction of electric power consumption.

It is preferable that the gas sensor constructed as described above further comprises an auxiliary pumping means including an auxiliary pumping electrode formed in the vicinity of the detecting electrode, for pumping-processing the predetermined gas component contained in the measurement gas after being pumping processed by the main pumping means, on the basis of a voltage applied between the auxiliary pumping electrode and the reference electrode.

Accordingly, at first, the measurement gas, which has been subjected to coarse adjustment for the predetermined gas component to have the predetermined concentration by the aid of the main pumping means, is further subjected to fine adjustment for the concentration of the predetermined gas component by the aid of the auxiliary pumping means. During the period in which the foregoing operation is performed, when the concentration of the predetermined gas component in the measurement gas in the external space is greatly changed (for example, oxygen concentration is changed from 0 to 20%), then the concentration distribution of the predetermined gas component in the measurement gas introduced into the main pumping means is greatly changed, and the amount of the predetermined gas component introduced into the measuring pumping means or the concentration-detecting means is also changed.

The concentration of the predetermined gas component in the measurement gas after being pumping-processed by the main pumping means is finely adjusted by the pumping process effected by the auxiliary pumping means. However, owing to the pumping process performed by the main pumping means, the change in concentration of the predetermined gas component in the measurement gas introduced into the auxiliary pumping means is greatly reduced as compared with the change in concentration of the predetermined gas component in the measurement gas from the external space (measurement gas introduced into the main pumping means). Accordingly, it is possible to accurately and constantly control the concentration of the predetermined gas component in the vicinity of the detecting electrode of the measuring pumping means or in the vicinity of the detecting electrode of the concentration-detecting means.

Therefore, the concentration of the predetermined gas component introduced into the measuring pumping means or the concentration-detecting means is scarcely affected by the change in concentration of the predetermined gas component in the measurement gas (measurement gas introduced into the main pumping means). As a result, the pumping current value detected by the current-detecting means or the electromotive force detected by the voltage-detecting means is not affected by the change in concentration of the predetermined gas component in the measurement gas, which has a value accurately corresponding to the amount of the objective component existing in the measurement gas.

The impedance between the electrodes except for the detecting electrode, which is detected by the impedance-detecting means, may be an impedance between the reference electrode and any one of the electrodes (the inner pumping electrode or the outer pumping electrode) of the main pumping means, or the impedance may be an impedance between the reference electrode and the auxiliary pumping electrode of the auxiliary pumping means. Alternatively, it is allowable to detect an impedance between the auxiliary electrode and any one of the electrodes of the main pumping means.

Especially, according to the invention described above, it is possible to more accurately control the temperature in the vicinity of the detecting electrode in the sensor element. Accordingly, it is possible to effectively suppress variation in detection output (the pumping current value or the electromotive force) which would be otherwise caused depending on the temperature of the measurement gas. Thus, it is possible to realize improvement in detection accuracy and improvement in reliability of the gas sensor.

The main pumping means may comprise the inner pumping electrode and the outer pumping electrode formed at the inside and outside of a first chamber surrounded by substrates composed of solid electrolytes for introducing the measurement gas thereinto, and the substrate interposed between the both electrodes.

The measuring pumping means may comprise the detecting electrode formed at the inside of a second chamber surrounded by substrates composed of solid electrolytes for introducing the measurement gas after being pumping-processed by the main pumping means thereinto, the reference electrode formed in a reference gas-introducing chamber surrounded by substrates composed of solid electrolytes for introducing a reference gas thereinto, and the substrate interposed between the detecting electrode and the reference electrode.

The concentration-detecting means may comprise the detecting electrode formed at the inside of a second chamber surrounded by substrates composed of solid electrolytes for introducing the measurement gas after being pumping-processed by the main pumping means thereinto, the reference electrode formed in a reference gas-introducing chamber surrounded by substrates composed of solid electrolytes for introducing a reference gas thereinto, and the substrate interposed between the detecting electrode and the reference electrode.

Preferably, the gas sensor constructed as described above may further comprise a first diffusion rate-determining section provided at a passage to introduce the measurement gas from the external space into the first chamber, for giving a predetermined diffusion resistance to the measurement gas, and a second diffusion rate-determining section provided at a passage to introduce the measurement gas after being pumping-processed by the main pumping means into the second chamber, for giving a predetermined diffusion resistance to the measurement gas.

Preferably, the gas sensor may further comprise a third diffusion rate-determining section provided at a passage for the measurement gas to enter the detecting electrode in the second chamber, for giving a predetermined diffusion resistance to the measurement gas.

The above and other objects, features and advantages of the present invention will become more apparent from the following description when taken in conjunction with the accompanying drawings in which a preferred embodiment of the present invention is shown by way of illustrative example.

BRIEF DESCRIPTION OF THE DRAWINGS

FIG. 5 shows the dependency on the measurement gas temperature of the output characteristic concerning Example having the same system as that of the gas sensor according to the first embodiment and Comparative Example based on the use of the conventional constant resistance control method.

FIG. 7A shows a waveform illustrating a case in which the level of a deviation signal is higher than the apex level of the triangular wave.

FIG. 7B shows a waveform illustrating a base-driving signal obtained under the condition shown in FIG. 7A.

FIG. 8A shows a waveform illustrating a case in which the level of a deviation signal is between the middle point level and the apex level of the triangular wave.

FIG. 8B shows a waveform illustrating a base-driving signal obtained under the condition shown in FIG. 8A.

FIG. 11 shows a circuit diagram illustrating a second modified embodiment of the gas sensor according to the first embodiment, especially illustrating an arrangement of a heater control circuit of a heater control system.

FIG. 14 shows a characteristic curve illustrating an output characteristic of the gas sensor according to the third embodiment.

DESCRIPTION OF THE PREFERRED EMBODIMENTS

Explanation will be made below with reference to FIGS. 1 to 17 for several illustrative embodiments in which the gas sensor according to the present invention is applied to gas sensors for measuring oxides such as NO, $NO_2$, $SO_2$, $CO_2$, and $H_2O$ contained in, for example, atmospheric air and exhaust gas discharged from vehicles or automobiles, and inflammable gases such as CO and CnHm.

Figure 1:
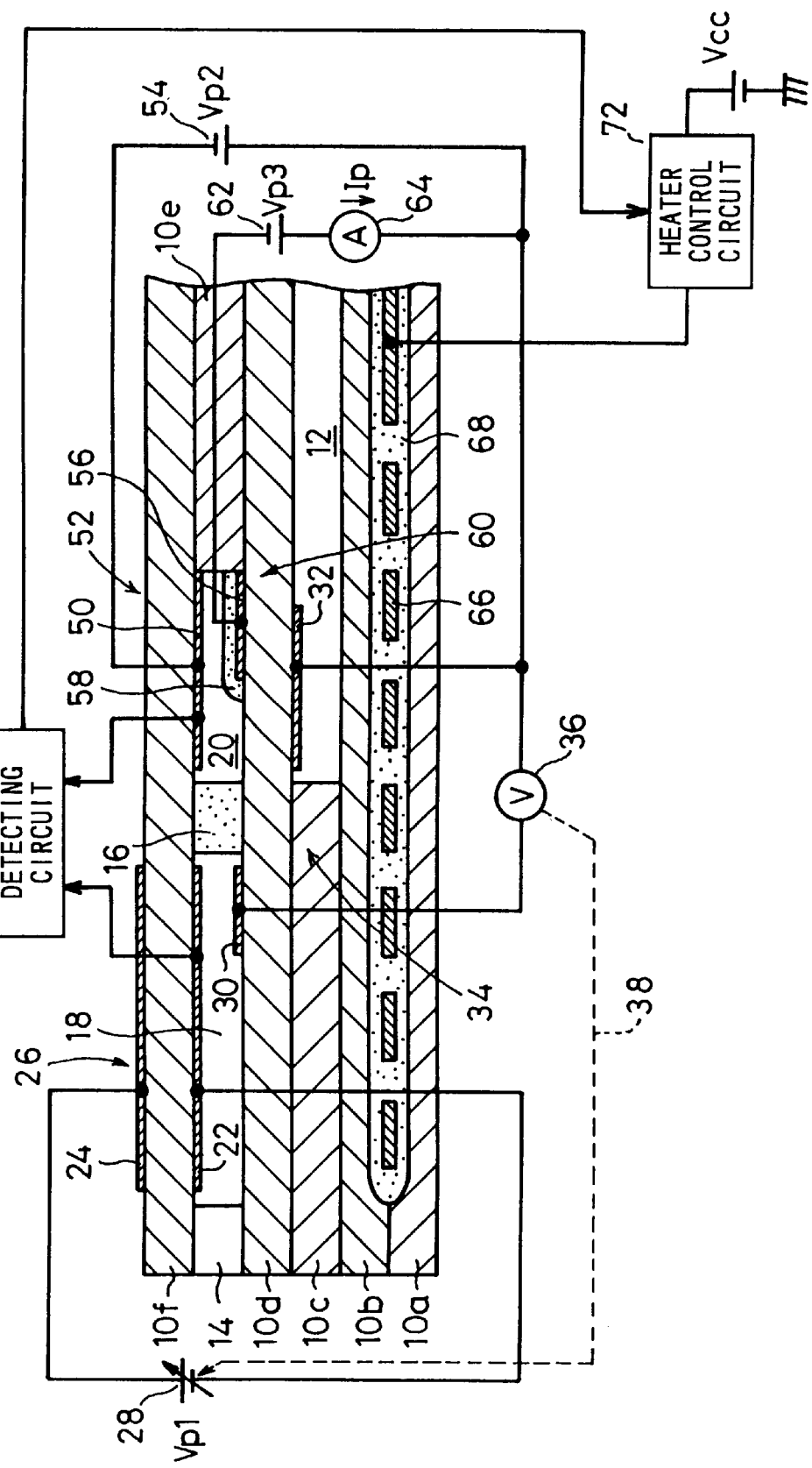
FIG. 1 shows an arrangement of a gas sensor according to a first embodiment.

At first, as shown in FIG. 1, a gas sensor according to the first embodiment has a substrate, wherein the overall substrate is comprised of six stacked solid electrolyte layers 10a to 10f composed of ceramics based on the use of oxygen ion-conductive solid electrolytes such as $ZrO_2$. First and second layers from the bottom are designated as first and second substrate layers 10a, 10b respectively. Third and fifth layers from the bottom are designated as first and second spacer layers 10c, 10e respectively. Fourth and sixth layers from the bottom are designated as first and second solid electrolyte layers 10d, 10f respectively.

Specifically, the first spacer layer 10c is stacked on the second substrate layer 10b. The first solid electrolyte layer 10d, the second spacer layer 10e, and the second solid electrolyte layer 10f are successively stacked on the first spacer layer 10c.

A space (reference gas-introducing space) 12, into which a reference gas such as atmospheric air to be used as a reference for measuring oxides is introduced, is formed between the second substrate layer 10b and the first solid electrolyte layer 10d, the space 12 being comparted by a lower surface of the first solid electrolyte layer 10d, an upper surface of the second substrate layer 10b, and side surfaces of the first spacer layer 10c.

The second spacer layer 10e is interposed between the first and second solid electrolyte layers 10d, 10f. First and second diffusion rate-determining sections 14, 16 are also interposed between the first and second solid electrolyte layers 10d, 10f.

A first chamber 18 for adjusting the partial pressure of oxygen in a measurement gas is formed and comparted by a lower surface of the second solid electrolyte layer 10f, side surfaces of the first and second diffusion rate-determining sections 14, 16, and an upper surface of the first solid electrolyte layer 10d. A second chamber 20 for finely adjusting the partial pressure of oxygen in the measurement gas and measuring oxides, for example, nitrogen oxides (NOx) in the measurement gas is formed and comparted by a lower surface of the second solid electrolyte layer 10f, a side surface of the second diffusion rate-determining section 16, a side surface of the second spacer layer 10e, and an upper surface of the first solid electrolyte layer 10d.

The external space communicates with the first chamber 18 via the first diffusion-rate determining section 14, and the first chamber 18 communicates with the second chamber 20 via the second diffusion rate-determining section 16.

The first and second diffusion-rate determining sections 14, 16 give predetermined diffusion resistances to the measurement gas to be introduced into the first and second chambers 18, 20 respectively. Each of the first and second diffusion-rate determining sections 14, 16 can be formed as a passage composed of, for example, a porous material, or a small hole having a predetermined cross-sectional area so that the measurement gas may be introduced.

Especially, the second diffusion-rate determining section 16 is arranged and filled with a porous material comprising, for example, $ZrO_2$. The diffusion resistance of the second diffusion-rate determining section 16 is made larger than the diffusion resistance of the first diffusion-rate determining section 14.

The atmosphere in the first chamber 18 is introduced into the second chamber 20 under the predetermined diffusion resistance via the second diffusion rate-determining section 16.

An inner pumping electrode 22 having a substantially rectangular planar configuration and composed of a porous cermet electrode is formed on the entire lower surface portion for forming the first chamber 18, of the lower surface of the second solid electrolyte layer 10f. An outer pumping electrode 24 is formed on a portion corresponding to the inner pumping electrode 22, of the upper surface of the second solid electrolyte layer 10f. An electrochemical pumping cell, i.e., a main pumping cell 26 is constructed by the inner pumping electrode 22, the outer pumping electrode 24, and the second solid electrolyte layer 10f interposed between the both electrodes 22, 24.

A desired control voltage (pumping voltage) Vp1 is applied between the inner pumping electrode 22 and the outer pumping electrode 24 of the main pumping cell 26 by the aid of an external variable power source 28 to allow a pumping current to flow in a positive or negative direction between the outer pumping electrode 24 and the inner pumping electrode 22. Thus, the oxygen in the atmosphere in the first chamber 18 can be pumped out to the external space, or the oxygen in the external space can be pumped into the first chamber 18.

A measuring electrode 30 having a substantially rectangular planar configuration and composed of a porous cermet electrode is formed on an upper surface portion for forming the first chamber 18 adjacent to the second diffusion rate-determining section 16, of the upper surface of the first solid electrolyte layer 10d. A reference electrode 32 is formed on a portion exposed to the reference gas-introducing space 12, of the lower surface of the first solid electrolyte layer 10d. An electrochemical sensor cell, i.e., an oxygen partial pressure-detecting cell 34 is constructed by the measuring electrode 30, the reference electrode 32, and the first solid electrolyte layer 10d.

An electromotive force is generated between the measuring electrode 30 and the reference electrode 32 on the basis of a difference in oxygen concentration between the atmosphere in the first chamber 18 and the reference gas (atmospheric air) in the reference gas-introducing space 12. The oxygen partial pressure-detecting cell 34 makes it possible to detect the partial pressure of oxygen in the atmosphere in the first chamber 18 by measuring the generated electromotive force by using a voltmeter 36.

The detected value of the partial pressure of oxygen is used to feedback-control the variable power source 28. Specifically, the pumping operation performed by the main pumping cell 26 is controlled so that the partial pressure of oxygen in the atmosphere in the first chamber 18 has a predetermined value which is sufficiently low to control the partial pressure of oxygen in the second chamber 20 in the next step.

Figure 2:
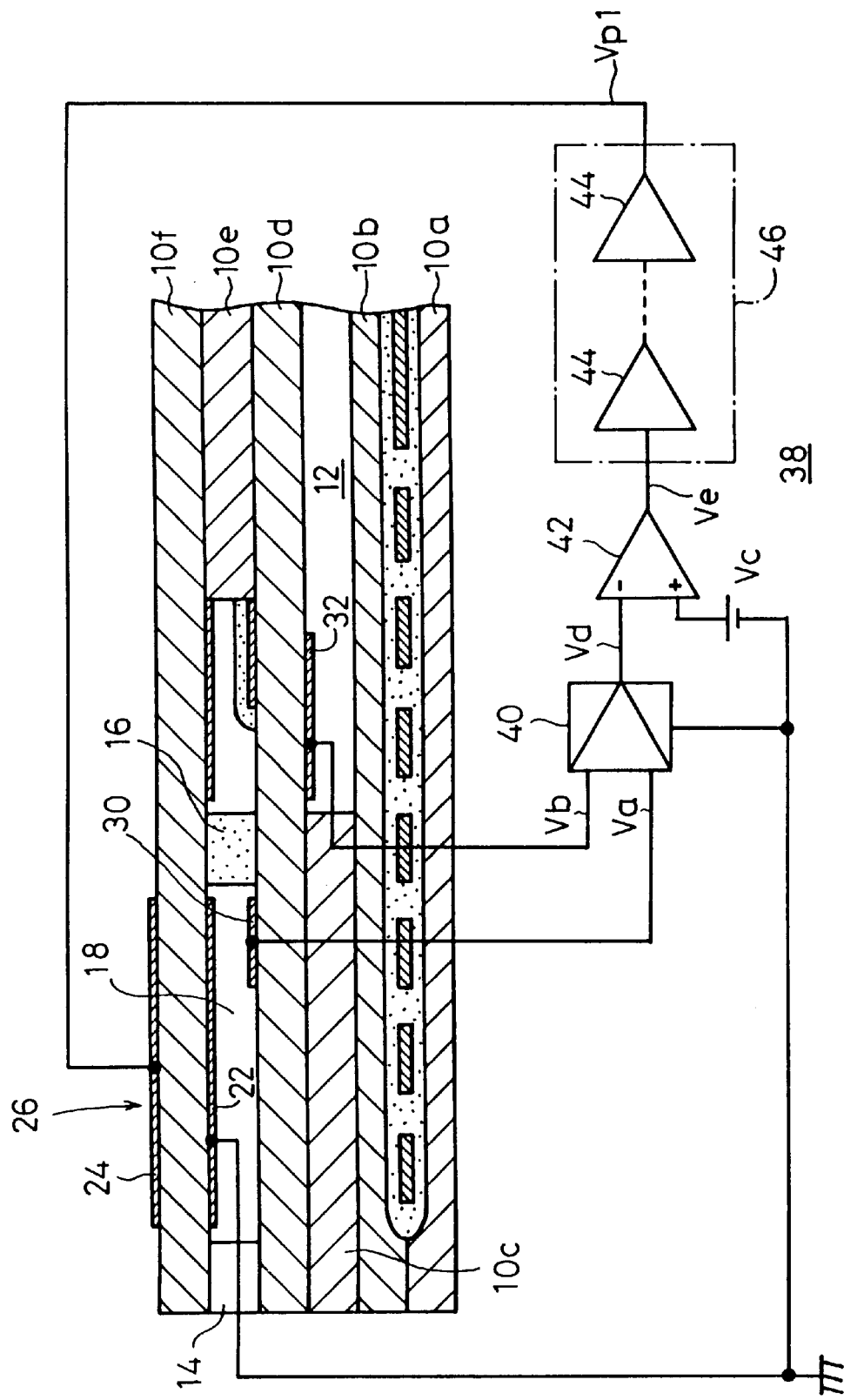
FIG. 2 shows an arrangement of a feedback control system for a main pumping cell of the gas sensor according to the first embodiment.

Specifically, as shown in FIG. 2, a circuit system (feedback control system) 38 for performing the feedback control comprises a first differential amplifier 40 for determining a difference between a difference (measured voltage Va) between an electric potential of the measuring electrode 30 and the ground electric potential and a difference (reference voltage Vb) between an electric potential of the reference electrode 32 and the ground electric potential, and amplifying the determined difference with a predetermined gain to make an output; a second differential amplifier 42 for determining a difference between the output of the first differential amplifier 40 and a reference voltage Vc, and amplifying the determined difference with a predetermined gain to make an output; and a signal-amplifying system 46 composed of a one-stage or multi-stage amplifier 44 for amplifying the output of the second differential amplifier 42 with a predetermined gain. In this embodiment, the wiring connection is made so that the output of the signal-amplifying system 46 is supplied to the outer pumping electrode 24 of the main pumping cell 26, and the inner pumping electrode 22 is grounded.

Accordingly, at first, the measurement gas is introduced into the first chamber 18 via the first diffusion rate-determining section 14. The measured voltage Va and the reference voltage Vb at that time are supplied to the first differential amplifier 40. The first differential amplifier 40 outputs the differential voltage Vd between the measured voltage Va and the reference voltage Vb. The differential voltage Vd is applied, for example, to an inverting terminal of the second differential amplifier 42 disposed at the downstream stage. The second differential amplifier 42 determines the difference between the differential voltage Vd supplied to the inverting terminal and the reference voltage Vc supplied to a non-inverting terminal. The voltage signal Ve, which is obtained by amplifying the determined difference with the predetermined gain, is outputted from an output terminal of the second differential amplifier 42. The voltage signal Ve is amplified with the predetermined gain by the signal-amplifying system 46 disposed at the downstream stage, and an obtained voltage is supplied as the pumping voltage Vp1 to the outer pumping electrode 24 of the main pumping cell 26. In this embodiment, the inner pumping electrode 22 has the ground electric potential (0 V). Therefore, the voltage between the both electrodes 22, 24 of the main pumping cell 26 is equivalent to the pumping voltage Vp1 supplied from the signal-amplifying system 46 after all.

Therefore, the main pumping cell 26 pumps out or pumps in oxygen in an amount corresponding to the level of the pumping voltage Vp1, of the measurement gas introduced into the first chamber 18. The oxygen concentration in the first chamber 18 is subjected to feedback control to give a predetermined level by repeating the series of operations described above.

The porous cermet electrode for constructing the inner pumping electrode 22 and the outer pumping electrode 24 is composed of a metal such as Pt and a ceramic such as $ZrO_2$. However, it is necessary, for the inner pumping electrode 22 and the measuring electrode 30 arranged in the first chamber 18 contacting with the measurement gas, to use a material having a weak reducing ability or no reducing ability with respect to the NO component in the measurement gas. It is preferable that the inner pumping electrode 22 and the measuring electrode 30 are composed of, for example, a compound having the perovskite structure such as $La_3CuO_4$, a cermet comprising a ceramic and a metal having a low catalytic activity such as Au, or a cermet comprising a ceramic, a metal of the Pt group, and a metal having a low catalytic activity such as Au. Further, when an alloy comprising Au and a metal of the Pt group is used as an electrode material, it is preferable to add Au in an amount of 0.03 to 35 vol % of the entire metal components.

On the other hand, as shown in FIG. 1, an auxiliary pumping electrode 50 having a substantially rectangular planar configuration and composed of a porous cermet electrode is formed on the entire lower surface portion for forming the second chamber 20, of the lower surface of the second solid electrolyte layer 10f. An auxiliary electrochemical pumping cell, i.e., an auxiliary pumping cell 52 is constructed by the auxiliary pumping electrode 50, the reference electrode 32, the second solid electrolyte layer 10f, the second spacer layer 10e, and the first solid electrolyte layer 10d.

A desired constant voltage Vp2 is applied between the reference electrode 32 and the auxiliary pumping electrode 50 of the auxiliary pumping cell 52 by the aid of an external power source 54. Thus, the oxygen in the atmosphere in the second chamber 20 can be pumped out to the reference gas-introducing space 12. Accordingly, the partial pressure of oxygen in the atmosphere in the second chamber 20 is allowed to have a low value of partial pressure of oxygen at which the measurement of the amount of the objective component is not substantially affected, under the condition in which the measurement gas component (NOx) is not substantially reduced or decomposed. In this embodiment, owing to the operation of the main pumping cell 26 for the first chamber 18, the change in amount of oxygen introduced into the second chamber 20 is greatly reduced as compared with the change in the measurement gas. Accordingly, the partial pressure of oxygen in the second chamber 20 is accurately controlled to be constant.

In the gas sensor according to the first embodiment, a detecting electrode 56 having a substantially rectangular planar configuration and composed of a porous cermet electrode is formed at a portion separated from the second diffusion rate-determining section 16, on an upper surface portion for forming the second chamber 20, of the upper surface of the first solid electrolyte layer 10d. An alumina film for constructing a third diffusion rate-determining section 58 is formed so that the detecting electrode 56 is covered therewith. An electrochemical pumping cell, i.e., a measuring pumping cell 60 is constructed by the detecting electrode 56, the reference electrode 32, and the first solid electrolyte layer 10d.

The detecting electrode 56 is composed of a porous cermet comprising zirconia as a ceramic and Rh as a metal capable of reducing NOx as the measurement gas component. Accordingly, the detecting electrode 56 functions as an NOx-reducing catalyst for reducing NOx existing in the atmosphere in the second chamber 20. Further, the oxygen in the atmosphere in the second chamber 20 can be pumped out to the reference gas-introducing space 12 by applying a constant voltage Vp3 between the detecting electrode 56 and the reference electrode 32 by the aid of a DC power source 62. The pumping current Ip, which is allowed to flow in accordance with the pumping operation performed by the measuring pumping cell 60, is detected by an ammeter 64.

The constant voltage (DC) power source 62 can apply a voltage of a magnitude to give a limiting current to the pumping for oxygen produced during decomposition in the measuring pumping cell 60 under the inflow of NOx restricted by the third diffusion rate-determining section 58.

The gas sensor according to the first embodiment further comprises a heater 66 for generating heat in accordance with electric power supply from the outside. The heater 66 is embedded in a form of being vertically interposed between the first and second substrate layers 10a, 10b. The heater 66 is provided in order to increase the conductivity of oxygen ion. A ceramic layer 68 composed of alumina or the like is formed to cover upper and lower surfaces of the heater 66 so that the heater 66 is electrically insulated from the substrate layers 10a, 10b.

As shown in FIG. 1, the heater 66 is arranged over the entire portion ranging from the first chamber 18 to the second chamber 20. Accordingly, each of the first chamber 18 and the second chamber 20 is heated to a predetermined temperature. Simultaneously, each of the main pumping cell 26, the oxygen partial pressure-detecting cell 34, the auxiliary pumping cell 52, and the measuring pumping cell 60 is also heated to a predetermined temperature and maintained at that temperature.

The gas sensor according to the first embodiment includes a heater control system comprising an impedance-detecting circuit 70 inserted and connected between, for example, the inner pumping electrode 22 of the main pumping cell 26 and the auxiliary pumping electrode 50 except for the detecting electrode 56, for detecting the impedance between the both electrodes 22, 50, and a heater control circuit 72 for controlling electric power application to the heater 66 on the basis of a detection signal supplied from the impedance-detecting circuit 70.

Figure 3:
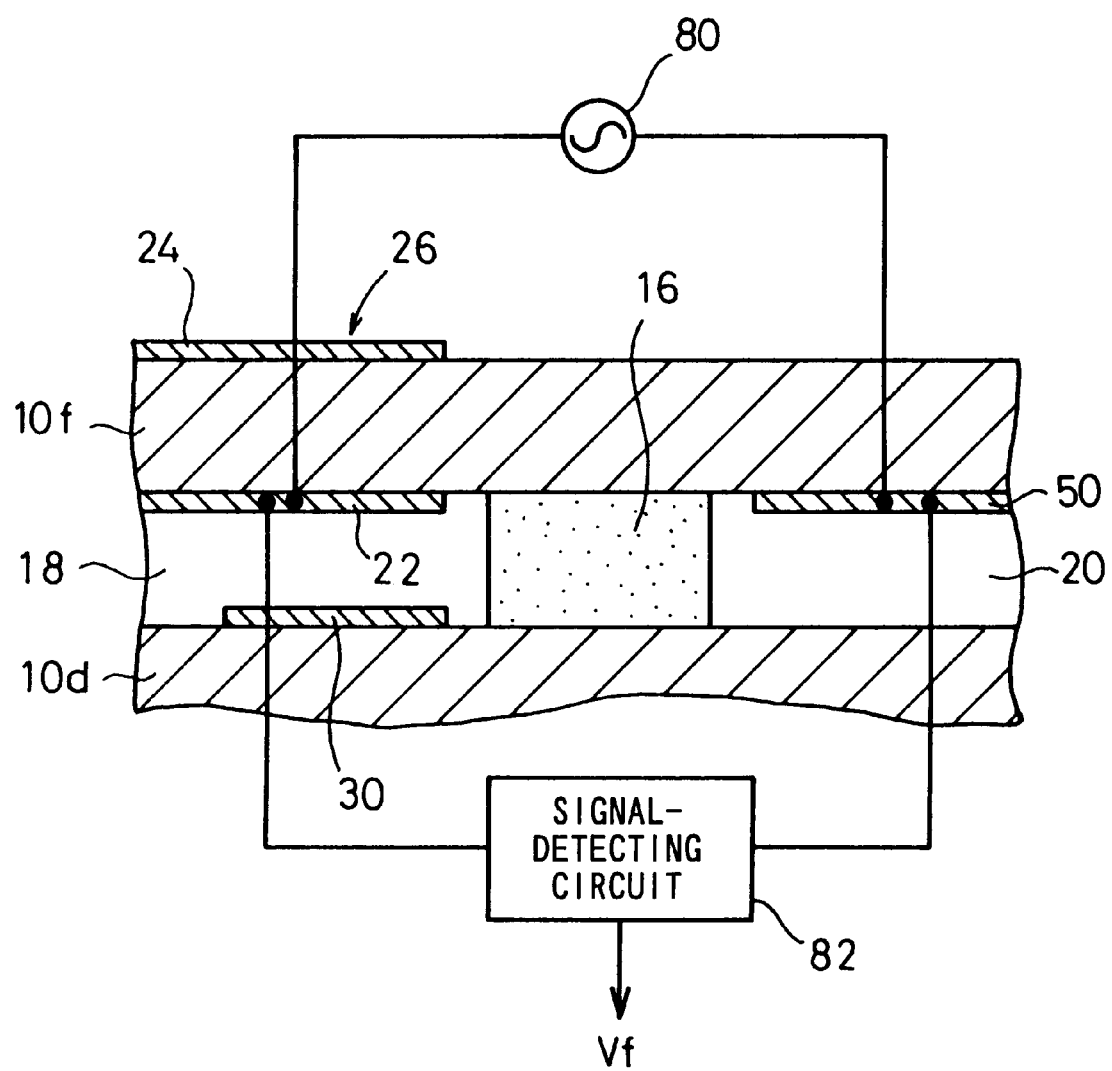
FIG. 3 shows a heater control system of the gas sensor according to the first embodiment.

As shown in FIG. 3, the impedance-detecting circuit 70 includes an alternating current-generating circuit 80 for supplying an alternating current between the inner pumping electrode 22 and the auxiliary pumping electrode 50, and a signal-detecting circuit 82 for detecting a voltage signal Vf at a level corresponding to the impedance between the electrodes 22, 50, generated between the electrodes 22, 50 in accordance with the alternating current supply between the electrodes 22, 50.

Figure 4:
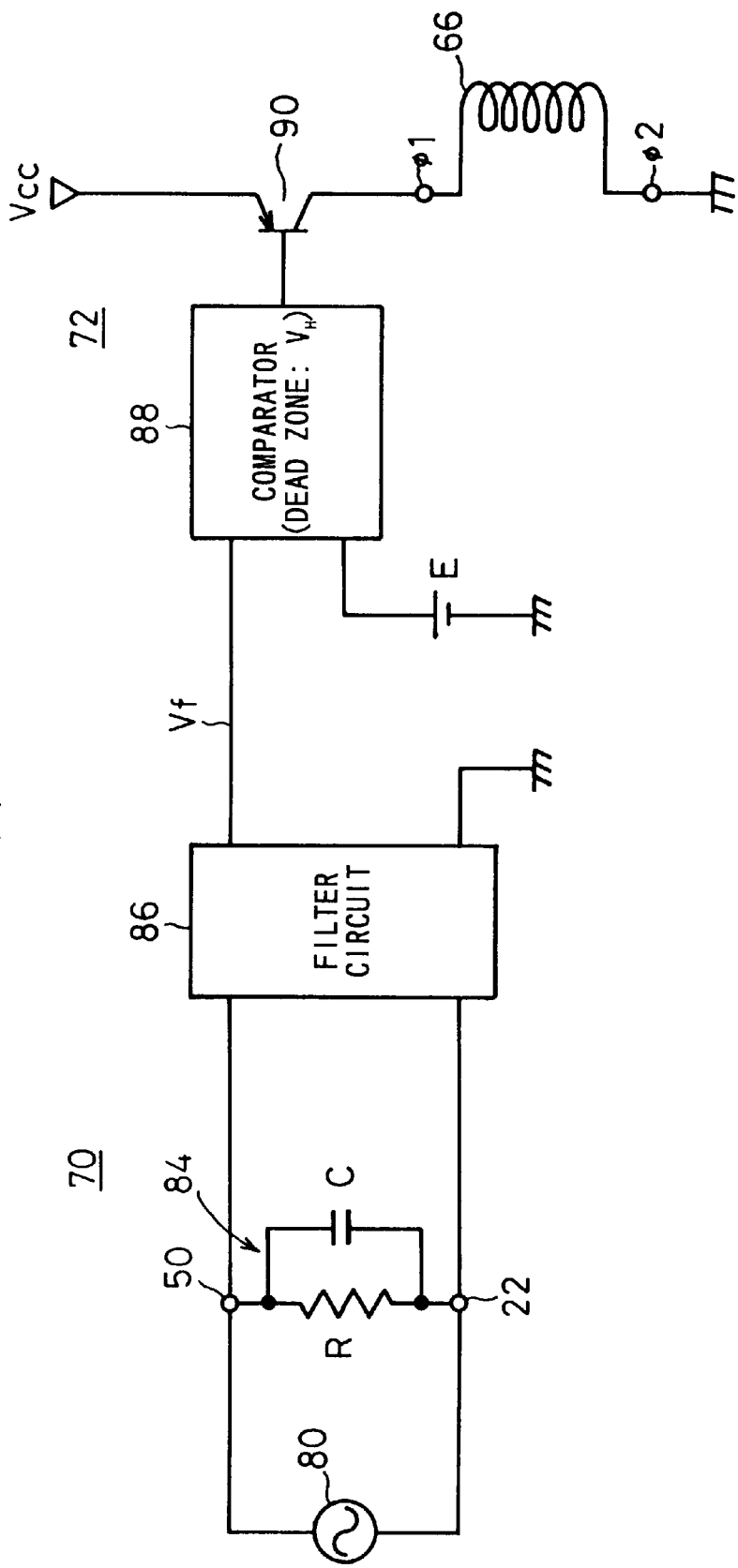
FIG. 4 shows a circuit diagram illustrating a specified example of the heater control system.

As shown in FIG. 4, the impedance measurement objective, which is constructed by the inner pumping electrode 22, the auxiliary pumping electrode 50, and the second solid electrolyte layer 10f interposed between the both electrodes 22, 50, is equivalently represented by a circuit 84 comprising a resistor R and a capacitor C connected in parallel.

Therefore, as shown in FIG. 4, the signal-detecting circuit 82 may be constructed by a filter circuit (for example, a low-pass filter and a band-pass filter) 86 for converting the alternating current signal generated between the electrodes 22, 50 into the voltage signal Vf at a level (hereinafter simply referred to as "detection level") corresponding to the impedance between the electrodes 22, 50.

On the other hand, as also shown in FIG. 4, the heater control circuit 72 is constructed as having a comparator 88 with hysteresis, and a pnp-type power transistor 90. The comparator 88 with hysteresis is operated as follows. That is, assuming that the reference level is E, and the dead zone level is $V_H$, if the detection level of the voltage signal Vf outputted from the filter circuit 86 is higher than a positive threshold level ($E+V_H/2$), then a low level signal is outputted, while if the detection level is lower than a negative threshold level ($E-V_H/2$), then a high level signal is outputted. If the detection level is within a range of $-V_H/2$ to $+V_H/2$, the present level is maintained.

The power transistor 90 has its collector terminal to which a power source Vcc is connected, its base terminal to which an output side of the comparator 88 with hysteresis is connected, and its emitter terminal to which a first terminal $\phi 1$ of the heater 66 is connected. A second terminal $\phi 2$ of the heater 66 is grounded.

The power transistor 90 is ON-operated by supplying the low level signal from the comparator 88 to the base terminal. Accordingly, the driving current is supplied from the power source Vcc to the heater 66. On the other hand, the power transistor 90 is OFF-operated by supplying the high level signal from the comparator 88 to the base terminal. Accordingly, the supply of the driving current to the heater 66 is stopped.

The frequency band of the alternating current component generated by the alternating current-generating circuit 80 is desirably set, for example, to be within a range of about 300 Hz to 100 kHz, and optimally within a range of 1 kHz to 10 kHz. The voltage of the alternating current component is desirably set to be at a level at which no trouble occurs in the function of each electrode, for example, not more than ±500 mV, and optimally about ±100 mV to ±300 mV.

The reference level E, which is supplied to the comparator 88 of the heater control circuit 72, is set to be the same level as the detection level obtained when the temperature of the measurement gas in the sensor element is at a predetermined temperature (desired temperature).

Next, the operation of the gas sensor according to the first embodiment will be explained. At first, the forward end of the gas sensor is disposed in the external space. Accordingly, the measurement gas is introduced into the first chamber 18 under the predetermined diffusion resistance via the first diffusion rate-determining section 14. The measurement gas, which has been introduced into the first chamber 18, is subjected to the pumping operation for oxygen, caused by applying the predetermined pumping voltage Vp1 between the outer pumping electrode 24 and the inner pumping electrode 22 which construct the main pumping cell 26. The partial pressure of oxygen is controlled to be a predetermined value, for example, $10^{-7}$ atm. The control is performed by the aid of the feedback control system 38 shown in FIG. 2.

The first diffusion rate-determining section 14 serves to limit the amount of diffusion and inflow of oxygen in the measurement gas into the measuring space (first chamber 18) when the pumping voltage Vp1 is applied to the main pumping cell 26 so that the current flowing through the main pumping cell 26 is suppressed.

In the first chamber 18, a state of partial pressure of oxygen is established, in which NOx in the atmosphere is not reduced by the inner pumping electrode 22 and the measuring electrode 30 in an environment of being heated by the external measurement gas and being heated by the heater 66. For example, a condition of partial pressure of oxygen is formed, in which the reaction of NO→$1/2N_2$+$1/2O_2$ does not occur, because of the following reason. That is, if NOx in the measurement gas (atmosphere) is reduced in the first chamber 18, it is impossible to accurately measure NOx in the second chamber 20 disposed at the downstream. In this context, it is necessary to establish a condition in the first chamber 18 in which NOx is not reduced by the component which participates in reduction of NOx (in this case, the metal component of the inner pumping electrode 22 and the measuring electrode 30). Specifically, such a condition is achieved by using, for the inner pumping electrode 22 and the measuring electrode 30, a material having a low ability to reduce NOx, for example, an alloy of Au and Pt.

The gas in the first chamber 18 is introduced into the second chamber 20 under the predetermined diffusion resistance via the second diffusion rate-determining section 16. The gas, which has been introduced into the second chamber 20, is subjected to the pumping operation for oxygen, caused by applying the predetermined constant voltage Vp2 between the reference electrode 32 and the auxiliary pumping electrode 50 which constitute the auxiliary pumping cell 52 to make fine adjustment so that the partial pressure of oxygen has a constant and low value of partial pressure of oxygen.

The second diffusion rate-determining section 16 serves to limit the amount of diffusion and inflow of oxygen in the measurement gas into the measuring space (second chamber 20) when the constant voltage Vp2 is applied to the auxiliary pumping cell 52 so that the current flowing through the auxiliary pumping cell 52 is suppressed, in the same manner as performed by the first diffusion rate-determining section 14.

In the second chamber 20, a state of partial pressure of oxygen is also established, in which NOx in the atmosphere is not reduced by the auxiliary pumping electrode 50 in an environment of being heated by the external measurement gas and being heated by the heater 66, in the same manner as established in the first chamber 18. Accordingly, it is also necessary for the auxiliary pumping electrode 50 to use a material having a weak reducing ability or no reducing ability with respect to the NO component in the measurement gas, in the same manner as the inner pumping electrode 22 and the measuring electrode 30. It is preferable that the auxiliary pumping electrode 50 is composed of, for example, a compound having the perovskite structure such as $La_3CuO_4$, a cermet comprising a ceramic and a metal having a low catalytic activity such as Au, or a cermet comprising a ceramic, a metal of the Pt group, and a metal having a low catalytic activity such as Au. Further, when an alloy comprising Au and a metal of the Pt group is used as an electrode material, it is preferable to add Au in an amount of 0.03 to 35 vol % of the entire metal components.

The measurement gas, which has been controlled for the partial pressure of oxygen in the second chamber 20 as described above, is introduced into the detecting electrode 56 under the predetermined diffusion resistance via the third diffusion rate-determining section 58.

When it is intended to control the partial pressure of oxygen in the atmosphere in the first chamber 18 to have a low value of the partial pressure of oxygen which does not substantially affect the measurement of NOx, by operating the main pumping cell 26, in other words, when the pumping voltage Vp1 of the variable power source 28 is adjusted by the aid of the feedback control system 38 so that the voltage detected by the oxygen partial pressure-detecting cell 34 is constant, if the oxygen concentration in the measurement gas greatly changes, for example, in a range of 0 to 20%, then the respective partial pressures of oxygen in the atmosphere in the second chamber 20 and in the atmosphere in the vicinity of the detecting electrode 56 slightly change in ordinary cases. This phenomenon is caused probably because of the following reason. That is, when the oxygen concentration in the measurement gas increases, the distribution of the oxygen concentration occurs in the widthwise direction and the thickness direction over the measuring electrode 30 in the first chamber 18. The distribution of the oxygen concentration changes depending on the oxygen concentration in the measurement gas.

However, in the case of the gas sensor according to the first embodiment, the auxiliary pumping cell 52 is provided for the second chamber 20 so that the partial pressure of oxygen in its internal atmosphere always has a constant low value of the partial pressure of oxygen. Accordingly, even when the partial pressure of oxygen in the atmosphere introduced from the first chamber 18 into the second chamber 20 changes depending on the oxygen concentration in the measurement gas, the partial pressure of oxygen in the atmosphere in the second chamber 20 can be always made to have a constant low value, owing to the pumping operation performed by the auxiliary pumping cell 52. As a result, the partial pressure of oxygen can be controlled to have a low value at which the measurement of NOx is not substantially affected.

NOx in the measurement gas introduced into the detecting electrode 56 is reduced or decomposed around the detecting electrode 56. Thus, for example, a reaction of NO→$1/2N_2$+ $1/2O_2$ is allowed to occur. In this process, a predetermined voltage Vp3, for example, 430 mV (700° C.) is applied between the detecting electrode 56 and the reference electrode 32 for constructing the measuring pumping cell 60, in a direction to pump out the oxygen from the second chamber 20 to the reference gas-introducing space 12.

Therefore, the pumping current Ip flowing through the measuring pumping cell 60 has a value which is proportional to a sum of the oxygen concentration in the atmosphere introduced into the second chamber 20, i.e., the oxygen concentration in the second chamber 20 and the oxygen concentration produced by reduction or decomposition of NOx by the aid of the detecting electrode 56.

In this embodiment, the oxygen concentration in the atmosphere in the second chamber 20 is controlled to be constant by means of the auxiliary pumping cell 52. Accordingly, for example, as shown in FIG. 5, the pumping current Ip flowing through the measuring pumping cell 60 is proportional to the NOx concentration. The NOx concentration corresponds to the amount of diffusion of NOx limited by the third diffusion rate-determining section 58. Therefore, even when the oxygen concentration in the measurement gas greatly changes, it is possible to accurately measure the NOx concentration, based on the use of the measuring pumping cell 60 by the aid of the ammeter 64.

It is assumed, for example, that the partial pressure of oxygen in the atmosphere in the second chamber 20 controlled by the auxiliary pumping cell 52 is 0.02 ppm, and the concentration of NO as the NOx component in the measurement gas is 100 ppm. The pumping current Ip flows in an amount corresponding to a sum (=50.02 ppm) of an oxygen concentration of 50 ppm produced by reduction or decomposition of NO and the oxygen concentration of 0.02 ppm in the atmosphere in the second chamber 20. Therefore, almost all of the pumping current value obtained by operating the measuring pumping cell 60 represents the amount brought about by the reduction or decomposition of NO. Accordingly, the obtained result does not depend on the oxygen concentration in the measurement gas.

During the period in which the foregoing operation is performed, the impedance between the inner pumping electrode 22 and the auxiliary pumping electrode 50 except for the detecting electrode 56 is detected as a voltage level by the aid of the impedance-detecting circuit 70. The electric power application to the heater 66 is controlled on the basis of the detected voltage level by the aid of the heater control circuit 72.

Specifically, if the temperature of the measurement gas becomes lower than the predetermined temperature, and the impedance between the electrodes 22, 50 is increased, then the level of the voltage signal Vf outputted from the filter circuit 86 (see FIG. 4) of the impedance-detecting circuit 70 is also increased. If the level of the voltage signal Vf becomes higher than the positive threshold level $(E+V_H/2)$ of the comparator 88, then the low level signal is supplied to the base electrode of the power transistor 90 included in the heater control circuit 72, and the electric power application to the heater 66 is started. Accordingly, the temperature of the measurement gas in the sensor element is gradually increased.

On the other hand, if the temperature of the measurement gas becomes higher than the predetermined temperature, and the impedance between the electrodes 22, 50 is decreased, then the level of the voltage signal Vf outputted from the filter circuit 86 is also decreased. If the level of the voltage signal Vf becomes lower than the negative threshold level $(E-V_H/2)$ of the comparator 88, then the high level signal is supplied to the base electrode of the power transistor 90 included in the heater control circuit 72, and the electric power application to the heater 66 is stopped. Accordingly, the temperature of the measurement gas in the sensor element is gradually decreased. As described above, the temperature in the sensor element can be maintained to be constant by controlling the electric power application to the heater 66 on the basis of the impedance value.

Now, an illustrative example will be described. This illustrative experiment concerns Example for a gas sensor constructed in the same manner as the gas sensor according to the first embodiment, and Comparative Example for a gas sensor based on the use of the conventional constant resistance control. The gas sensors concerning Example and Comparative Examples were placed in exhaust gas discharged from a diesel engine having a high oxygen concentration/high temperature gas region to observe the degree of variation in output characteristics in Example and Comparative Example depending on the high or low temperature of the measurement gas. Experimental results are shown in FIG. 5. Characteristic curves shown in FIG. 5 were obtained by plotting output characteristics obtained in Example and Comparative Example, while giving the NO concentration in the external space along the lower axis of abscissa, the detected current value obtained by the ammeter 64 along the axis of ordinate, and the measurement gas temperature during measurement along the upper axis of abscissa. In FIG. 5, solid circles represent the output characteristic obtained in Example, and solid squares represent the output characteristic obtained in Comparative Example.

According to the experimental results, the following fact can be understood. That is, in the case of Comparative Example, when the measurement gas temperature is lower than 600° C., it is possible to obtain the detected current value in conformity with the NO concentration. However, when the measurement gas temperature exceeds 600° C., a phenomenon occurs in which the detected current value makes shift. Specifically, a phenomenon occurs in which the detected current value increases to be higher than the prescribed detected current value expected on the basis of the concentration of the predetermined gas component, in accordance with the increase in temperature. On the other hand, in Example, the detected current value is obtained in conformity with the NO concentration up to 800° C., in which the characteristic is improved as compared with Comparative Example.

As described above, it is unnecessary for the gas sensor according to the first embodiment, as compared with the conventional constant resistance control method, to manufacture it as having a strict ratio between the resistance value of the lead section of the heater and the resistance value of the heat-generating section of the heater. Further, it is possible to avoid the influence which would be otherwise exerted by the temperature of the measurement gas due to the increase in resistance value of the heater lead section.

In the gas sensor according to the first embodiment, the impedance value between the electrodes except for the detecting electrode 56 is detected. Therefore, the voltage Vp3 applied to the measuring pumping cell 60 is free from variation which would be otherwise caused by the detection of the impedance. Accordingly, it is possible to suppress, for example, superimposition of noise and fluctuation of the pumping current Ip detected by the aid of the ammeter 64.

In other words, the gas sensor according to the first embodiment makes it possible to suppress variation in detection output which would be otherwise caused depending on the temperature of the measurement gas. Moreover, it is possible to realize a high S/N ratio of the detection output.

Especially, in the gas sensor according to the first embodiment, the impedance between the inner pumping electrode 22 and the auxiliary pumping electrode 50 is detected. Accordingly, the interior of the sensor element can be subjected to control while monitoring the temperature in the first chamber 18 and the temperature in the second chamber 20. Therefore, the measurement gas temperature in the vicinity of the detecting electrode 56 can be controlled more accurately. As a result, it is possible to effectively suppress variation in detection output (pumping current value) which would be otherwise caused depending on the measurement gas temperature, and it is possible to realize improvement in detection accuracy and improvement in reliability of the gas sensor.

Next, three modified embodiments of the gas sensor according to the first embodiment will be described with reference to FIGS. 6 to 11. Components or parts corresponding to those shown in FIGS. 1 and 4 are designated by the same reference numerals, duplicate explanation of which will be omitted.

At first, a gas sensor according to the first modified embodiment is constructed in approximately the same manner as the gas sensor according to the first embodiment (see FIGS. 1 and 4). However, the former is different from the latter in the arrangement of the heater control system.

Figure 6:
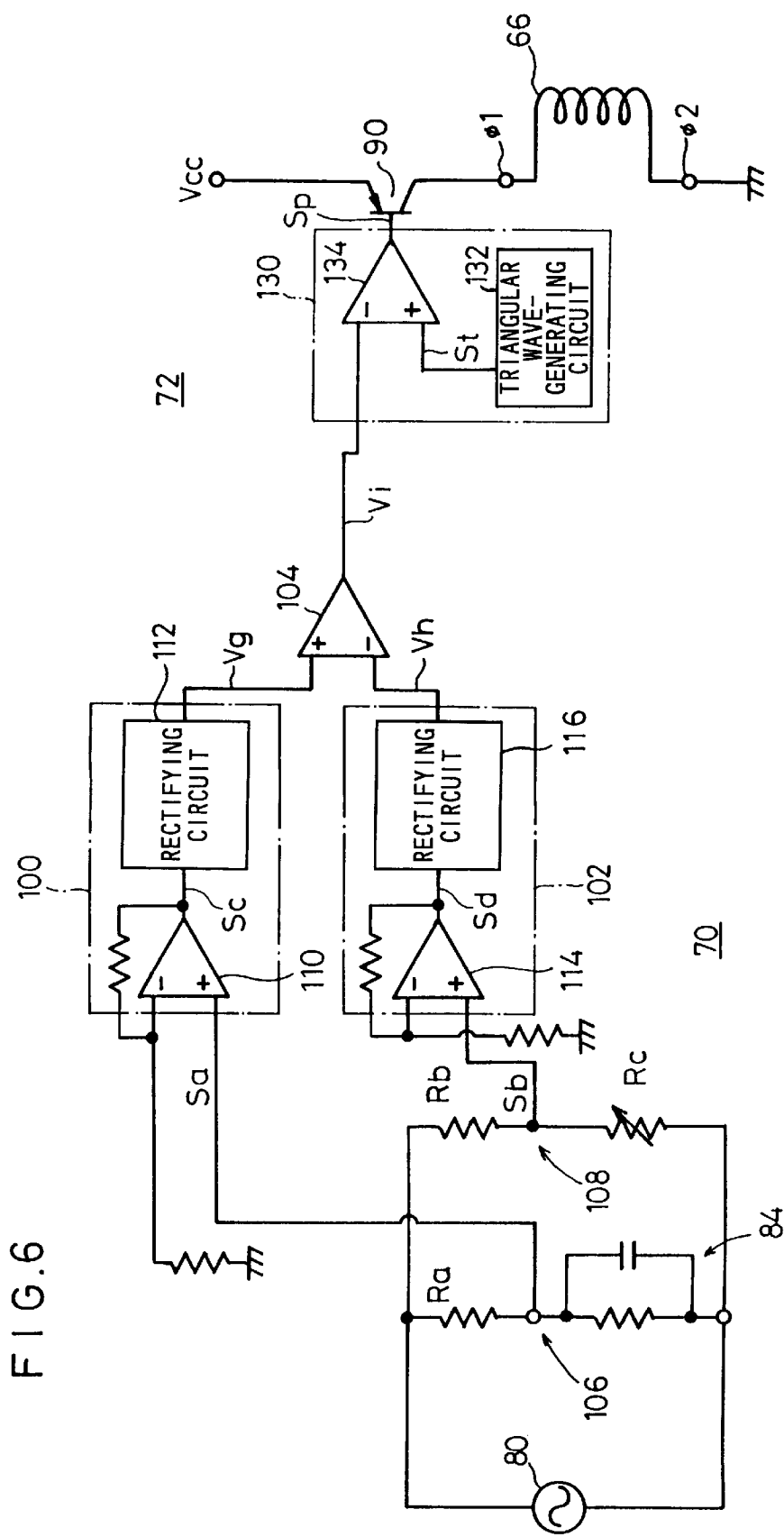
FIG. 6 shows a circuit diagram illustrating a first modified embodiment of the gas sensor according to the first embodiment, especially illustrating an arrangement of a heater control system.

That is, as shown in FIG. 6, the heater control system comprises the alternating current-generating circuit 80 as well as two detection circuits (first and second detection circuits 100, 102), a differential amplifier 104, and a pulse width-modulating circuit 130 for modulating the pulse width of the signal (hereinafter simply referred to as "base-driving signal Sp") for driving the base of the power transistor 90.

Specifically, at first, a first series circuit 106 comprising a fixed resistor Ra connected in series to the parallel circuit 84 including the resistor R and the capacitor C (the equivalent circuit of the impedance measurement objective constructed by the inner pumping electrode 22, the auxiliary pumping electrode 50, and the second solid electrolyte layer 10f disposed therebetween), and a second series circuit 108 comprising a fixed resistor Rb connected in series to a variable resistor Rc are connected in parallel between the supply line of the alternating current-generating circuit 80 respectively. The wiring connection is made such that an alternating current signal Sa, which is generated in the parallel circuit (element impedance) 84 by supplying the alternating current to the first and second series circuits 106, 108, is supplied to the first detection circuit 100. The wiring connection is made such that an alternating current signal Sb, which is generated in the variable resistor Rc, is supplied to the second detection circuit 102. Further, the wiring connection is made such that both of an output Vg of the first detection circuit 100 and an output Vh of the second detection circuit 102 are supplied to the differential amplifier 104 disposed at the downstream stage. FIG. 6 shows an example of wiring connection in which the output Vg of the first detection circuit 100 is inputted into a non-inverting input terminal of the differential amplifier 104, and the output Vh of the second detection circuit 102 is inputted into an inverting input terminal thereof.

The resistance value of the variable resistor Rc is set to be a resistance value corresponding to a normal impedance between the electrodes of the impedance measurement objective which is connected as the first series circuit 106. In this embodiment, the resistance value is set to be a resistance value corresponding to a normal impedance between the inner pumping electrode 22 and the auxiliary pumping electrode 50.

The first detection circuit 100 comprises, in connection, a non-inverting amplifying circuit 110 for amplifying, with a predetermined gain, the alternating current signal Sa generated in the parallel circuit (element impedance) 84, and a rectifying circuit 112 for rectifying an output Sc from the non-inverting amplifying circuit 110 and converting an obtained result into the voltage signal Vg at a direct current level corresponding to the output level. The second detection circuit 102 comprises, in connection, a non-inverting amplifying circuit 114 for amplifying, with a predetermined gain, the alternating current signal Sb generated in the variable resistor Rc, and a rectifying circuit 116 for rectifying an output Sd from the non-inverting amplifying circuit 114 and converting an obtained result into the voltage signal Vh at a direct current level corresponding to the output level. The fixed resistor Ra has the same resistance value as that of the fixed resistor Rb.

The pulse width-modulating circuit 130 comprises a triangular wave-generating circuit 132 for generating and outputting a predetermined triangular wave St having, for example, a bottom level of −5 V and an apex level of +5 V, and a comparator 134 for comparing the triangular wave St supplied from the triangular wave-generating circuit 132 with an output signal Vi supplied from the differential amplifier 104. FIG. 6 shows an example of wiring connection in which the output signal Vi supplied from the differential amplifier 104 is inputted into an inverting input terminal of the comparator 134, and the triangular wave St supplied from the triangular wave-generating circuit 132 is inputted into a non-inverting input terminal thereof.

Figure 9A:
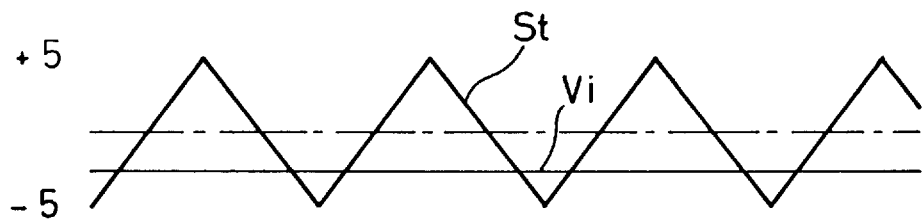
FIG. 9A shows a waveform illustrating a case in which the level of a deviation signal is between the bottom level and the middle point level of the triangular wave.
Figure 9B:
FIG. 9B shows a waveform illustrating a base-driving signal obtained under the condition shown in FIG. 9A.

The level of the output signal Vi from the differential amplifier 104 provides a threshold value for the triangular wave St. That is, if the level of the output signal Vi is not lower than the apex level of the triangular wave St as shown in FIG. 7A, the base-driving signal at a low level is always outputted from the comparator 134 as shown in FIG. 7B. If the level of the output signal Vi is higher than the bottom level of the triangular wave and lower than the apex level as shown in FIGS. 8A and 9A, then the base-driving signal is outputted at a high level during a period in which the triangular wave St is higher than the level of the output signal Vi, and the base-driving signal is outputted at a low level during a period in which the triangular wave St is lower than the level of the output signal Vi, as shown in FIGS. 8B and 9B.

Figure 10A:
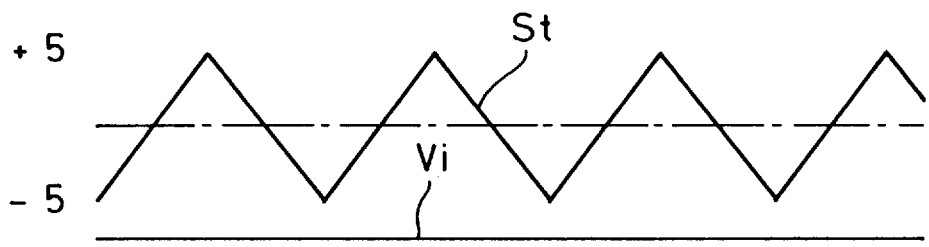
FIG. 10A shows a waveform illustrating a case in which the level of a deviation signal is lower than the bottom level of the triangular wave.
Figure 10B:
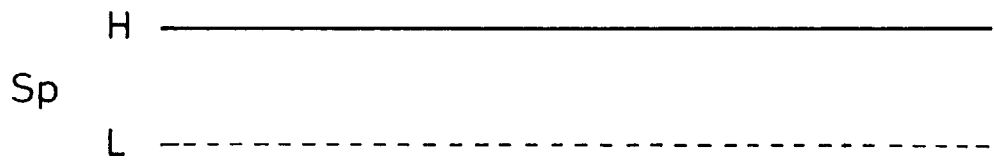
FIG. 10B shows a waveform illustrating a base-driving signal obtained under the condition shown in FIG. 10A.

If the level of the output signal Vi is not higher than the bottom level of the triangular wave as shown in FIG. 10A, the base-driving signal at a high level is always outputted from the comparator 134 as shown in FIG. 10B.

Next, the operation of the gas sensor according to the first modified embodiment, especially the operation of the heater control system will be explained. At first, the alternating current is supplied to the first series circuit 106 including the impedance measurement objective (parallel circuit) 84 by the aid of the alternating current-generating circuit 80, simultaneously with which the alternating current is also supplied to the second series circuit 108 including the variable resistor Rc set to have the resistance value corresponding to the normal impedance between the electrodes 22, 50.

When the alternating current is supplied to the first series circuit 106, the alternating current signal Sa generated in the parallel circuit 84 (element impedance) is supplied to the first detection circuit 100, and it is outputted after being converted into the direct current voltage signal Vg. On the other hand, when the alternating current is supplied to the second series circuit 108, the alternating current signal Sb generated in the variable resistor Rc is supplied to the second detection circuit 102, and it is outputted after being converted into the direct current voltage signal (reference signal) Vh.

Both of the voltage signal Vg outputted from the first detection circuit 100 and the reference signal Vh outputted from the second detection circuit 102 are supplied to the differential amplifier 104. The differential amplifier 104 determines a difference between the voltage signal Vg and the reference signal Vh to make an output as the deviation signal Vi.

The deviation signal Vi outputted from the differential amplifier 104, especially its voltage level is compared with the triangular wave St supplied from the triangular wave-generating circuit 132, by the aid of the comparator 134 included in the pulse width-modulating circuit 130 disposed at the downstream stage.

At first, during the warming-up period, the difference in temperature between the sensor element temperature and the measurement gas temperature is extremely large, and the impedance between the electrodes 22, 50 is extremely large. Accordingly, as shown in FIG. 7A, the level of the deviation signal Vi exceeds the apex level of the triangular wave St, and the base-driving signal Sp is always at a low level. As a result, the power transistor 90 is always turned ON, and the electric power is continuously applied to the heater 66. When the sensor element temperature is raised by the continuous electric power application to the heater 66, the level of the deviation signal Vi is lower than the apex level of the triangular wave St. Accordingly, the level of the deviation signal Vi varies within a range between the bottom level and the apex level depending on the high or low temperature of the measurement gas (see FIGS. 8A to 9B).

When the measurement gas temperature becomes lower than the predetermined temperature, and the impedance between the electrodes 22, 50 is increased, then the level of the deviation signal Vi outputted from the differential amplifier 104 of the impedance-detecting circuit 70 is also increased as shown in FIGS. 8A and 8B, and the width of the low level pulse of the base-driving signal Sp is widened in a degree corresponding to the foregoing increase. As a result, the period of time to apply the electric power to the heater 66 is prolonged, and the measurement gas temperature in the sensor element is gradually raised.

On the other hand, when the measurement gas temperature becomes higher than the predetermined temperature, and the impedance between the electrodes 22, 50 is decreased, then the level of the deviation signal Vi outputted from the differential amplifier 104 of the impedance-detecting circuit 70 is also decreased as shown in FIGS. 9A and 9B, and the width of the low level pulse of the base-driving signal Sp is narrowed in a degree corresponding to the foregoing decrease. As a result, the period of time to apply the electric power to the heater 66 is shortened, and the measurement gas temperature in the sensor element is gradually lowered.

As described above, the temperature in the sensor element can be maintained to be constant by controlling the electric power application to the heater 66 on the basis of the impedance value.

In the gas sensor according to the first modified embodiment, the target impedance value can be set by using the resistor (variable resistor Rc). Therefore, it is unnecessary to use, as the first and second detection circuits 100, 102 for converting the alternating current signal into the voltage signal, any circuit device having a complicated circuit arrangement such as a high-order low-pass filter and a band-pass filter based on the use of an operational amplifier. The system of the present invention can be realized by using simple components, for example, differential amplifiers, rectifying circuits based on the use of diodes and first-order CR low-pass filters. Thus, it is possible to effectively simplify the circuit arrangement and effectively reduce electric power consumption.

Next, a gas sensor according to the second modified embodiment will be explained with reference to FIG. 11. As shown in FIG. 11, the gas sensor according to the second modified embodiment is constructed in approximately the same manner as the gas sensor according to the first embodiment (see FIG. 4). However, the former is different from the latter in that a differential amplifier 118 is connected in place of the comparator 88 with hysteresis included in the heater control circuit 72. The power transistor 90 disposed at the downstream stage functions not as a digital switching circuit based on the use of the saturation region and the breaking region of the transistor, but as an analog current control circuit based on the use of the saturation region, the operating region, and the breaking region of the transistor.

That is, the gas sensor according to the second modified embodiment controls the measurement gas temperature in the sensor element by continuously controlling the amount of current supply on the basis of the change in impedance between the electrodes 22, 50 without stopping the electric power application to the heater 66. In this embodiment, it is possible to suppress excessive electric power consumption which would be otherwise observed upon the start of electric power application to the heater 66.

This embodiment illustrates wiring connection in which the deviation signal Vi from the differential amplifier 104 is supplied to the inverting terminal of the differential amplifier 118, and the reference level Ea is supplied to the non-inverting terminal thereof. In this process, the reference level Ea is set to be a level which is different from the reference level E shown in FIG. 4, because it is necessary to compare the reference level Ea with the level (deviation level) of the deviation signal Vi supplied from the differential amplifier 104. Specifically, the reference level Ea is set to be the same as the deviation level obtained when the measurement gas temperature in the sensor element is the predetermined temperature (desired temperature).

Next, although not shown, a gas sensor according to the third modified embodiment is constructed such that the impedance-detecting circuit 70 for the heater control system is the impedance-detecting circuit included in the gas sensor according to the first embodiment, i.e., the impedance-detecting circuit 70 based on the use of the filter circuit 86, and the heater control circuit 72 is the heater control circuit included in the gas sensor according to the second modified embodiment, i.e., the heater control circuit 72 based on the use of the differential amplifier 118.

In this embodiment, it is possible to obtain the gas sensor which involves, in combination, the effect of the gas sensor according to the first embodiment and the effect of the gas sensor according to the second modified embodiment.

Next, a gas sensor according to the second embodiment will be explained with reference to FIG. 12. Components or parts corresponding to those shown in FIG. 1 are designated by the same reference numerals, duplicate explanation of which will be omitted.

Figure 12:
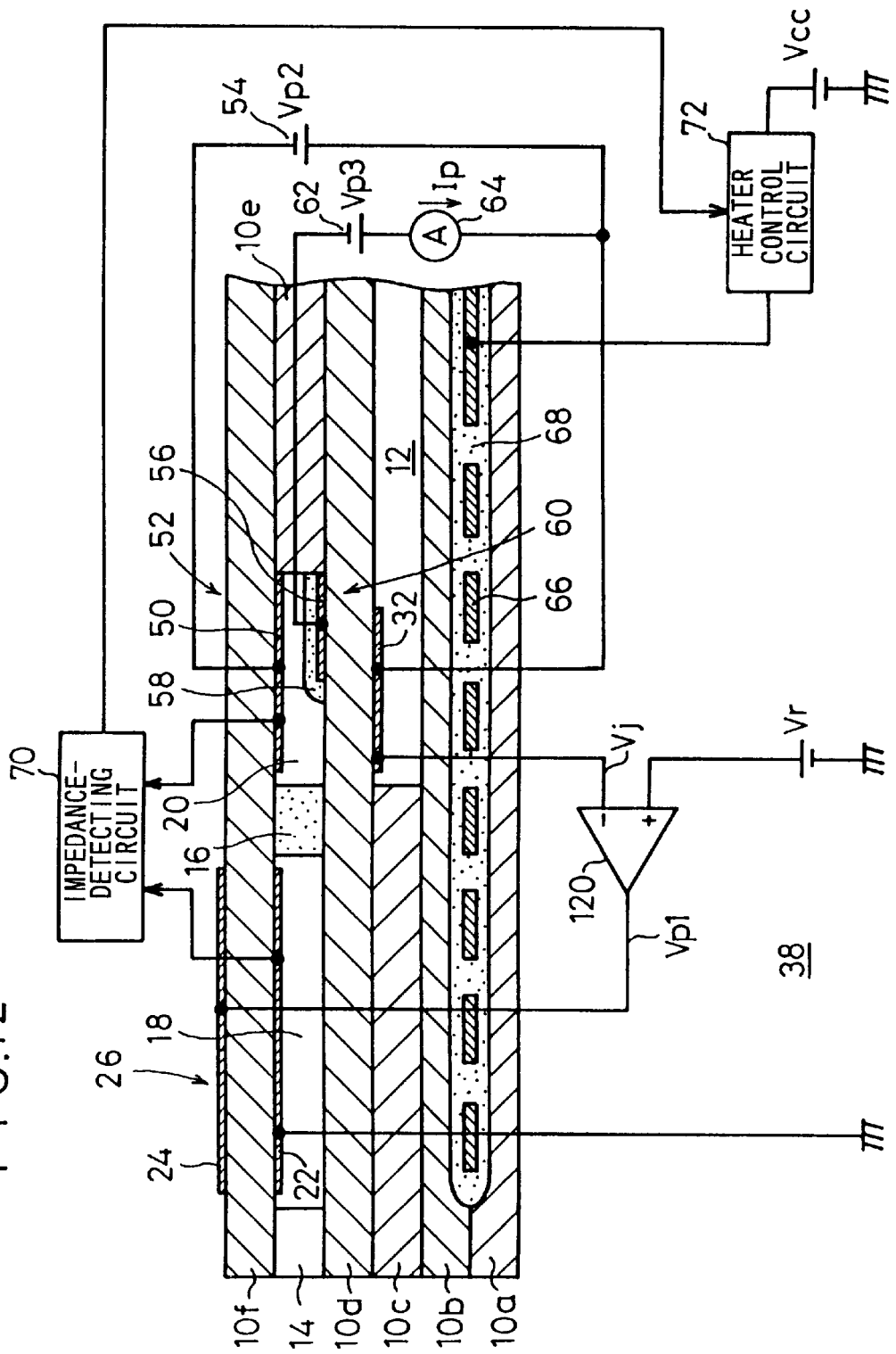
FIG. 12 shows an arrangement of a gas sensor according to a second embodiment.

As shown in FIG. 12, the gas sensor according to the second embodiment is constructed in approximately the same manner as the gas sensor according to the first embodiment (see FIG. 1). However, the former is different from the latter in that the feedback control system 38 for the main pumping cell 26 is constructed as follows.

That is, the feedback control system 38 includes a differential amplifier 120 for comparing a terminal voltage Vj between the reference electrode 32 and the inner pumping electrode 22 with a reference voltage Vr and amplifying an obtained difference with a predetermined gain to make an output, which is wired and connected such that the output voltage (differential voltage) from the differential amplifier 120 is applied, as the pumping voltage Vp1 to the main pumping cell 26, between the outer pumping electrode 24 and the inner pumping electrode 22. In this embodiment, the inner pumping electrode 22 is grounded.

Next, the operation of the gas sensor according to the second embodiment will be explained. At first, the measurement gas is introduced into the first chamber 18 via the first diffusion rate-determining section 14. During this process, the terminal voltage Vj, which is obtained between the inner pumping electrode 22 of the main pumping cell 26 and the reference electrode 32 formed on the side of the reference gas-introducing space 12, is applied, for example, to the non-inverting terminal of the differential amplifier 120. The differential amplifier 120 determines the difference between the terminal voltage Vj supplied to the inverting terminal and the reference voltage Vr supplied to the non-inverting terminal. The voltage Vp1, which is obtained by amplifying the difference with the predetermined gain, is outputted from the output terminal of the differential amplifier 120. The output voltage Vp1 is applied to the outer pumping electrode 24 of the main pumping cell 26. However, in this embodiment, the inner pumping electrode 22 is allowed to have the ground electric potential (0 V). Consequently, the voltage between the both electrodes 22, 24 of the main pumping cell 26 is equivalent to the output voltage Vp1 from the differential amplifier 120.

Therefore, the main pumping cell 26 functions as a pump for pumping out or pumping in the oxygen contained in the measurement gas introduced into the first chamber 18 in an amount corresponding to the level of the output voltage Vp1. The oxygen concentration in the first chamber 18 is feedback-controlled to arrive at a predetermined level by repeating the foregoing series of operations.

In this embodiment, the terminal voltage (measured voltage) Vj, which is applied to the inverting terminal of the differential amplifier 120, is the terminal voltage between the inner pumping electrode 22 of the main pumping cell 26 and the reference electrode 32 disposed in the reference gas-introducing space 12. Accordingly, when the amount of oxygen pumped out by the main pumping cell 26 is changed, and the concentration of oxygen in the first chamber 18 is changed, then the terminal voltage between the inner pumping electrode 22 of the main pumping cell 26 and the reference electrode 32 is changed without any time delay (changed in real-time). Therefore, it is possible to effectively suppress the oscillation phenomenon which would be otherwise caused in the feedback control system 38.

In the feedback control system 38 described above, the control voltage (output voltage Vp1) is feedback-controlled so that the terminal voltage Vj between the inner pumping electrode 22 and the reference electrode 32 is converged to the same level as that of the reference voltage Vr.

It is also possible for the gas sensor according to the second embodiment to adopt the arrangements of the first to third modified embodiments concerning the first embodiment.

Next, a gas sensor according to the third embodiment will be explained with reference to FIG. 13. Components or parts corresponding to those shown in FIG. 1 are designated by the same reference numerals, duplicate explanation of which will be omitted.

Figure 13:
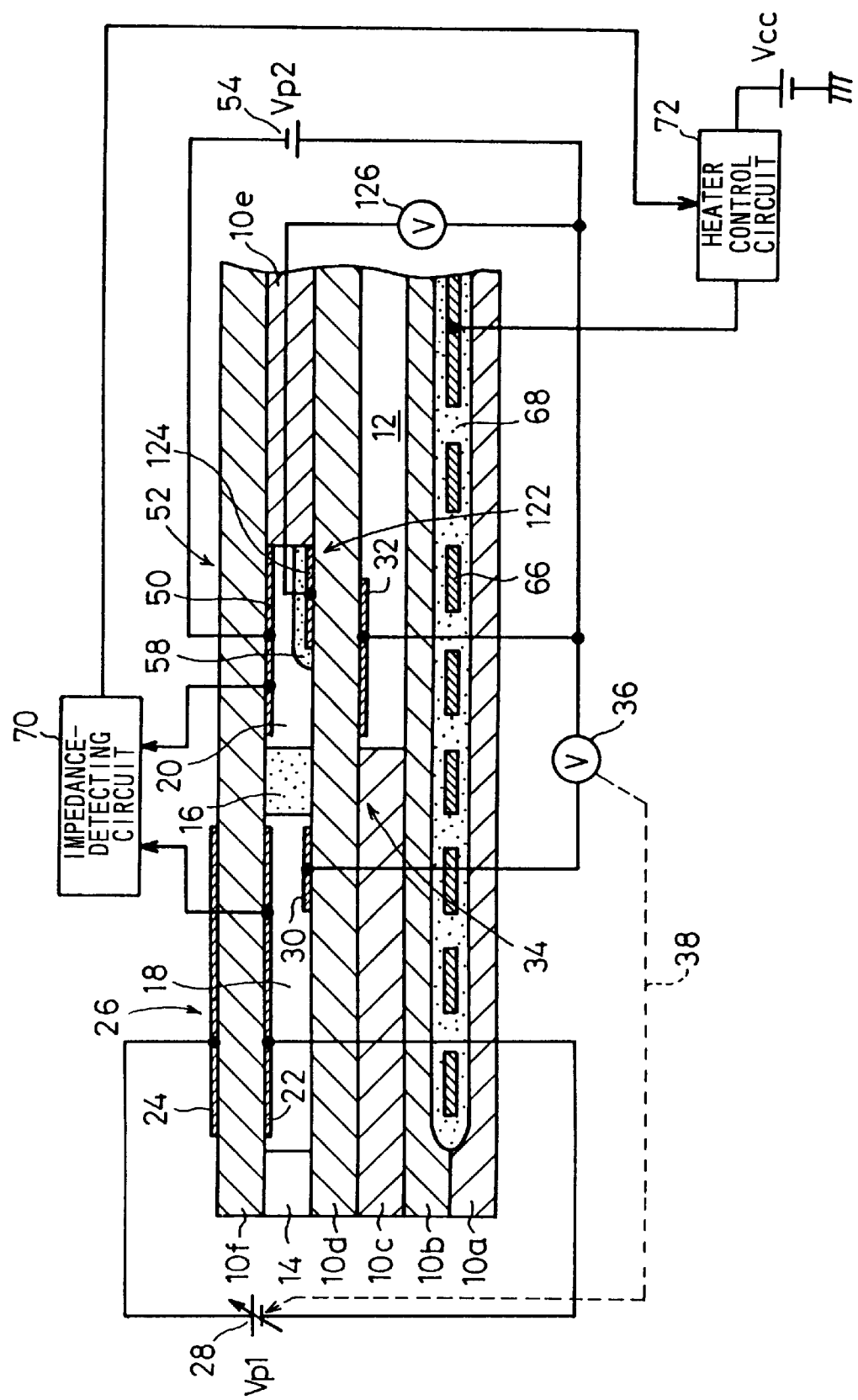
FIG. 13 shows an arrangement of a gas sensor according to a third embodiment.

As shown in FIG. 13, the gas sensor according to the third embodiment is constructed in approximately the same manner as the gas sensor according to the first embodiment (see FIG. 1). However, the former is different from the latter in that an oxygen partial pressure-detecting cell 122 is provided in place of the measuring pumping cell 60.

The oxygen partial pressure-detecting cell 122 comprises a detecting electrode 124 formed on the upper surface portion for forming the second chamber 20, of the upper surface of the first solid electrolyte layer 10d, the reference electrode 32 formed on the lower surface of the first solid electrolyte layer 10d, and the first solid electrolyte layer 10d interposed between the both electrodes 124, 32.

In this embodiment, an electromotive force (electromotive force of the oxygen concentration cell), which corresponds to the difference in oxygen concentration between the atmosphere around the detecting electrode 124 and the atmosphere around the reference electrode 32, is generated between the detecting electrode 124 and the reference electrode 32 of the oxygen partial pressure-detecting cell 122. Therefore, the partial pressure of oxygen in the atmosphere around the detecting electrode 124, in other words, the partial pressure of oxygen defined by the oxygen produced by reduction or decomposition of the measurement gas component (NOx) is detected as a voltage value by measuring the electromotive force generated between the detecting electrode 124 and the reference electrode 32 by using a voltmeter 126.

Now, the principle of detection performed by the gas sensor according to the third embodiment will be explained with reference to a characteristic curve shown in FIG. 14.

At first, when the NO concentration in the external space is 0 ppm, if the oxygen concentration in the atmosphere in the first chamber 18 is controlled by the aid of the feedback control system 38 so that the pumping voltage Vp1 for the main pumping cell 26 has a value ($10^{-7}$ atm) corresponding to 300 mV, then the oxygen concentration in the atmosphere in the second chamber 20 is also $10^{-7}$ atm. Thus, the electromotive force, which is generated between the detecting electrode 124 and the reference electrode 32 of the oxygen partial pressure-detecting cell 122 provided for the second chamber 20, is about 460 mV.

When the NO concentration in the external space is gradually increased, then the reducing or decomposing reaction of NO is caused on the detecting electrode 124, and the oxygen concentration in the atmosphere around the detecting electrode 124 is increased, because the detecting electrode 124 also functions as an NOx-reducing catalyst in the same manner as the detecting electrode 56 of the measuring pumping cell 60 described above (see FIG. 1). Accordingly, the electromotive force, which is generated between the detecting electrode 124 and the reference electrode 32, is gradually decreased. With reference to FIG. 14 illustrating the characteristic curve, for example, when the NO concentration increases to 300 ppm, 500 ppm, and 1000 ppm, the electromotive force detected by the voltmeter 126 is gradually decreased to 300 mV, 250 mV, and 220 mV respectively.

The degree of the decrease in electromotive force represents the NO concentration. In other words, the electromotive force, which is outputted from the oxygen partial pressure-detecting cell 122 for the second chamber 20, constructed by the detecting electrode 124, the reference electrode 32, and the first solid electrolyte layer 10d, represents the NO concentration in the measurement gas.

The gas sensor according to the third embodiment also includes the same heater control system as the heater control system according to the first embodiment, i.e., the impedance-detecting circuit 70 and the heater control circuit 72.

Therefore, in the gas sensor according to the third embodiment, it is unnecessary to manufacture the gas sensor as having a strict resistance ratio between the resistance value of the heater lead section and the resistance value of the heat-generating section of the heater, in the same manner as the gas sensor according to the first embodiment. Moreover, it is possible to avoid the influence of the temperature of the measurement gas, which would be otherwise exerted due to the increase in resistance value of the heater lead section.

In another viewpoint, the impedance value between the inner pumping electrode 22 and the auxiliary pumping electrode 50 is detected. Accordingly, the electromotive force, which is generated by the oxygen partial pressure-detecting cell 122, is free from variation which would be otherwise caused due to the detection of the impedance. Thus, it is possible to suppress, for example, superimposition of noise and fluctuation of the electromotive force (voltage) detected by the voltmeter 126.

Therefore, it is possible to suppress variation in detection output which would be otherwise caused depending on the temperature of the measurement gas. Moreover, it is possible to realize a high S/N ratio of the detection output.

Further, the temperature of the measurement gas in the vicinity of the detecting electrode 124 can be highly accurately controlled, and the variation of the detection output (electromotive force), which would be otherwise caused by the temperature of the measurement gas, can be effectively suppressed. These advantages result in improvement in detection accuracy of the gas sensor and improvement in reliability.

It is also possible for the gas sensor according to the third embodiment to adopt the arrangements of the first to third modified embodiments concerning the first embodiment.

Figure 15:
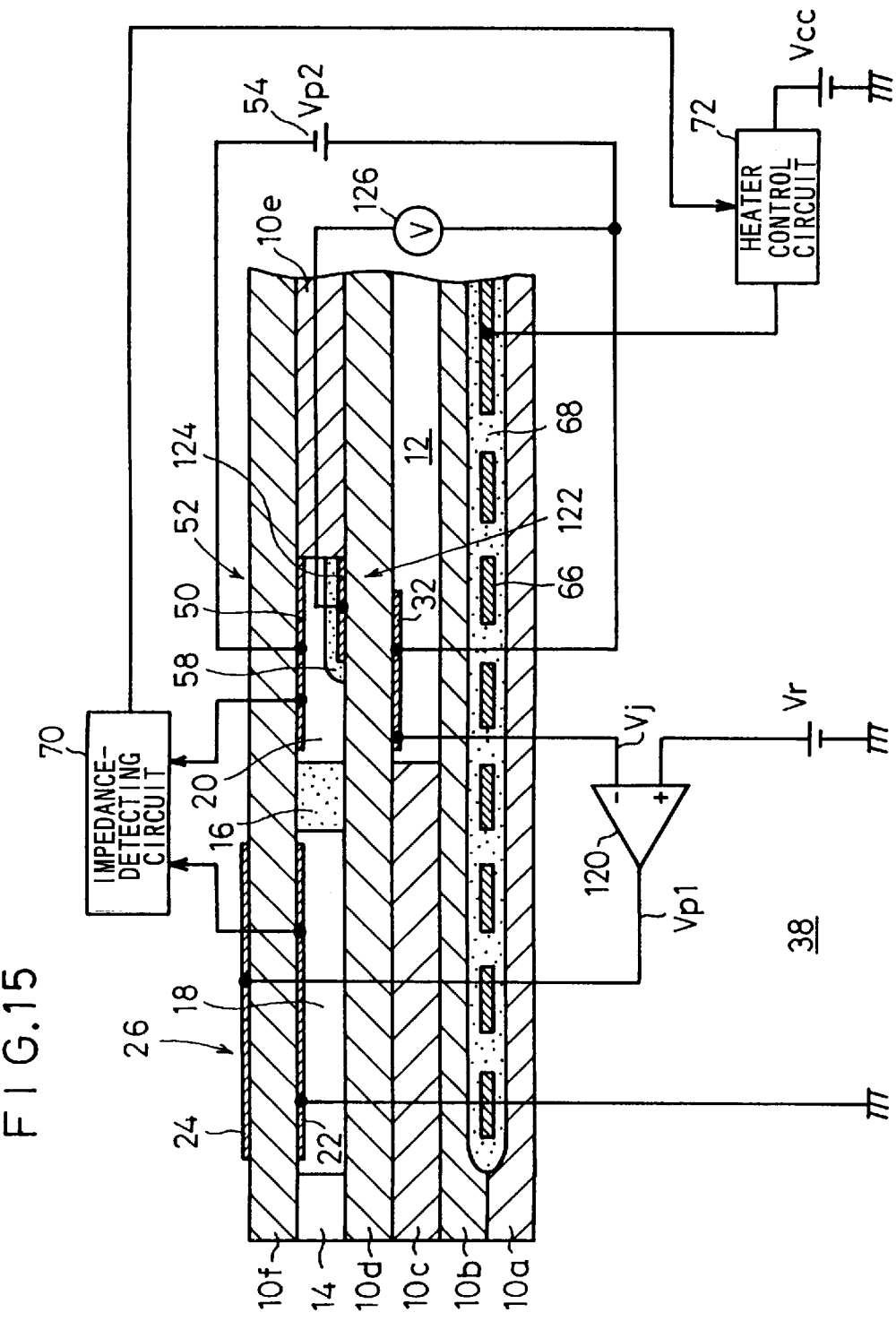
FIG. 15 shows an arrangement of a gas sensor according to a fourth embodiment.

Next, a gas sensor according to the fourth embodiment will be explained with reference to FIG. 15.

The gas sensor according to the fourth embodiment is constructed in the same manner as the gas sensor according to the third embodiment. However, the former is different from the latter in that the feedback control system 38 for the main pumping cell 26 is constructed in the same manner as that of the gas sensor according to the second embodiment. That is, the wiring connection is made such that the gas sensor includes the differential amplifier 120 for comparing the terminal voltage Vj between the reference electrode 32 and the inner pumping electrode 22 with the reference electrode Vr to obtain the difference which is amplified with the predetermined gain to make the output. Further, the output voltage (differential voltage) from the differential amplifier 120 is applied, as the pumping voltage Vp1 to the main pumping cell 26, between the outer pumping electrode 24 and the inner pumping electrode 22.

The gas sensor according to the fourth embodiment has the same effect as that of the gas sensor according to the third embodiment, and it further provides the effect of the gas sensor according to the second embodiment, i.e., the effect that the oscillation phenomenon in the feedback control system 38 can be effectively suppressed.

In the gas sensors according to the first to fourth embodiments (including the several modified embodiments), the impedance-detecting circuit 70 is used to detect the impedance between the inner pumping electrode 22 and the auxiliary pumping electrode 50 so that the measurement gas temperature in the sensor element is controlled. However, the measurement gas temperature in the sensor element may be controlled by detecting the impedance between the following electrodes:

(1) between the outer pumping electrode 24 and the auxiliary pumping electrode 50;
(2) between the reference electrode 32 and the auxiliary pumping electrode 50;
(3) between the inner pumping electrode 22 and the detecting electrode (56 or 124);
(4) between the outer pumping electrode 24 and the detecting electrode (56 or 124);
(5) between the inner pumping electrode 22 and the reference electrode 32 (see FIG. 16); and
(6) between the outer pumping electrode 24 and the reference electrode 32 (see FIG. 17).

Figure 16:
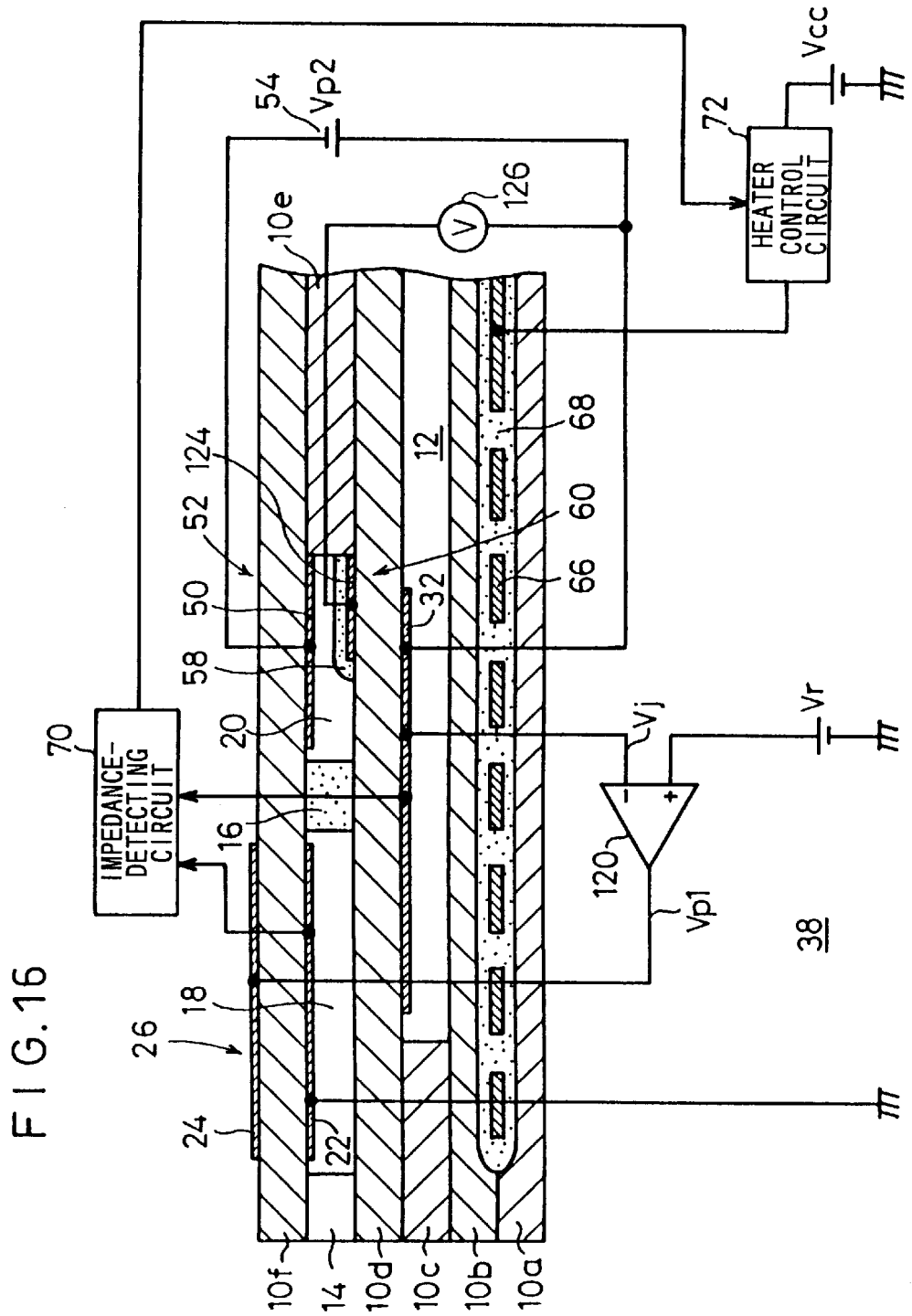
FIG. 16 shows an arrangement of a case in which an impedance between an inner pumping electrode and a reference electrode is detected.
Figure 17:
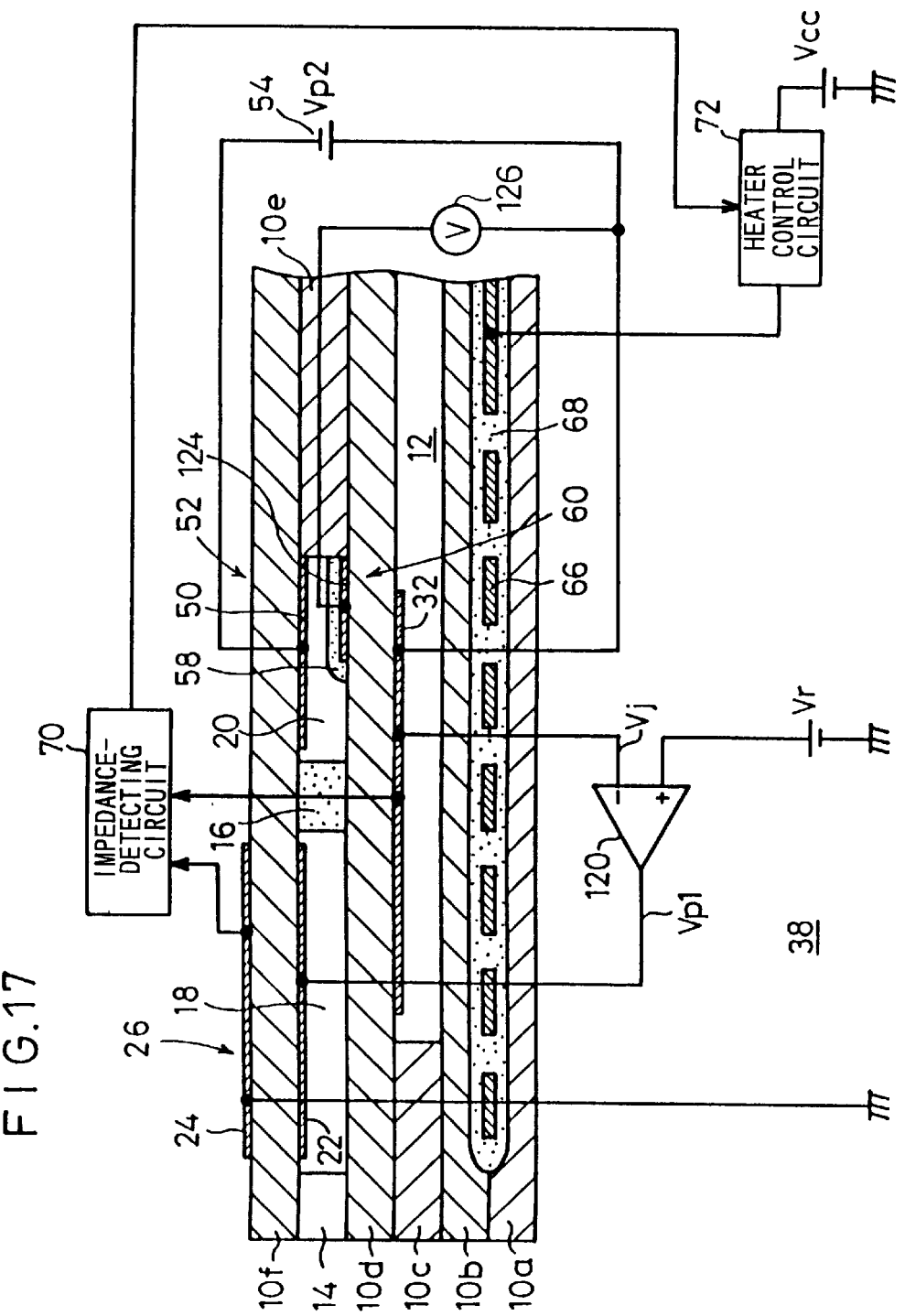
FIG. 17 shows an arrangement of a case in which an impedance between an outer pumping electrode and a reference electrode is detected.

Especially, in the cases of (5) and (6), as shown in FIGS. 16 and 17, the reference electrode 32, which is formed on the lower surface of the first solid electrolyte layer 10d, is formed to extend up to a position corresponding to the main pumping cell 26 (position under the main pumping cell 26). Alternatively, although not shown, it is preferable that the reference electrode 32 is formed at a position corresponding to the main pumping cell, of the lower surface of the first solid electrolyte layer 10d, in order to improve the detection accuracy for the impedance.

The gas sensors according to the first to fourth embodiments described above are directed to NOx as the measurement gas component. However, the present invention is also effectively applicable to the measurement of bound oxygen-containing gas components such as $H_2O$ and $CO_2$ other than NOx, in which the measurement is affected by oxygen existing in the measurement gas.

It is a matter of course that this invention is not limited to the embodiments described above, which may be constructed in other various forms without deviating from the gist or essential characteristics of this invention.

As explained above, the gas sensor according to the present invention comprises a main pumping means including a solid electrolyte contacting with an external space, and an inner pumping electrode and an outer pumping electrode formed on inner and outer surfaces of the solid electrolyte, for pumping-processing (pumping in and pumping out) a predetermined gas component contained in a measurement gas introduced from the external space, on the basis of a control voltage applied between the electrodes; a measuring pumping means including a solid electrolyte and a detecting electrode and a reference electrode formed on the solid electrolyte, for pumping-processing the predetermined gas component contained in the measurement gas after being pumping-processed by the main pumping means, on the basis of a voltage applied between the detecting electrode and the reference electrode; a current-detecting means for detecting a pumping current generated depending on an amount of the predetermined gas component pumping-processed by the measuring pumping means; a heater for heating at least the main pumping means and the measuring pumping means to a predetermined temperature; an impedance-detecting means for detecting an impedance between an electrode disposed on a side of the main pumping means and an electrode disposed on a side of the measuring pumping means; and a heater control means for controlling electric power application to the heater on the basis of a value of the impedance detected by the impedance-detecting means.

Accordingly, the following effects are obtained. That is, it is possible to suppress variation in detection output which would be otherwise caused depending on the temperature of the measurement gas. Further, it is possible to realize a high S/N ratio of the detection output. Especially, the impedance is detected between the electrode disposed on the side of the main pumping means and the electrode disposed on the side of the measuring pumping means. Therefore, it is possible to monitor the temperature on the side of the main pumping means and the temperature on the side of the measuring pumping means (or the concentration-detecting means) in the sensor element, and it is possible to highly accurately control the temperature in the sensor element.

Further, the impedance between the auxiliary pumping electrode of the auxiliary pumping means and the reference electrode, or the impedance between the inner pumping electrode of the main pumping means and the auxiliary pumping electrode may be detected as the impedance between the electrodes detected by the impedance-detecting means. By doing so, it is possible to highly accurately control the temperature of the measurement gas in the vicinity of the detecting electrode in the sensor element, and it is possible to further suppress output variation in detection output. Further, the alternating current-generating circuit may be wired and connected such that the alternating current is supplied not only between the foregoing electrodes but also to the resistor designed to have the resistance value corresponding to the normal impedance between the electrodes. Moreover, the signal-detecting circuit may comprise the first detection circuit for converting the alternating current generated between the electrodes into the voltage signal at the level corresponding to the impedance between the electrodes, the second detection circuit for converting the alternating current signal generated in the resistor into the voltage signal at the level corresponding to the impedance of the resistor to be used as the reference signal, and the differential circuit for determining the difference between the voltage signal outputted from the first detection circuit and the reference signal outputted from the second detection circuit to make the output as the deviation signal. By doing so, it is possible to obtain the inherent effect that the simplified control system can be achieved.

What is claimed is:

1. A gas sensor comprising:

a main pumping means including an inner pumping electrode and an outer pumping electrode located inside and outside of a first chamber formed in a substrate comprised of solid electrolyte, for pumping-processing a first predetermined gas component contained in a measurement gas introduced from said external space into said first chamber, on the basis of a control voltage applied between said electrodes;

an electric signal-generating conversion means including a detecting electrode and a reference electrode located inside and outside of a second chamber formed in said substrate, for generating, by conversion, an electric signal corresponding to an amount of a second predetermined gas component contained in said measurement gas after being pumping-processed by said main pumping means;

a heater for heating at least said main pumping means and said electric signal-generating conversion means to a predetermined temperature;

an impedance-detecting means for detecting an impedance between an electrode of said main pumping means and an electrode of said second chamber, said impedance detection means including an alternating current-generating circuit for supplying an alternating current between said electrodes subjected to said impedance detection; and a heater control means for controlling electric power application to said heater on the basis of a value of said impedance detected by said impedance-detecting means.

2. The gas sensor according to claim 1, wherein said electric signal-generating conversion means comprises:

a measuring pumping means including said solid electrolyte and a detecting electrode and a reference electrode located inside and outside of said second chamber, for pumping-processing said second predetermined gas component contained in said measurement gas after being pumping-processed by said main pumping means, on the basis of a voltage applied between said detecting electrode and said reference electrode; and a current-detecting means for detecting a pumping current generated depending on an amount of said second predetermined gas component pumping-processed by said measuring pumping means.

3. The gas sensor according to claim 2, wherein said measuring pumping means comprises:

said detecting electrode located at the inside of a second chamber in said substrate for introducing said measurement gas after being pumping-processed by said main pumping means thereinto;

said reference electrode located in a reference gas introducing chamber in said substrate for introducing a reference gas thereinto;

a solid electrolyte layer being interposed between said detecting electrode and said reference electrode.

4. The gas sensor according to claim 1, wherein said electric signal-generating conversion means comprises:

a concentration-detecting means including said solid electrolyte layer and a detecting electrode and a reference electrode located inside and outside of said second chamber, for generating an electromotive force corresponding to a difference between an amount of said second predetermined gas component contained in said measurement gas after being pumping-processed by said main pumping means and an amount of said predetermined gas component contained in a reference gas existing on a side of said reference electrode; and a voltage-detecting means for detecting said electromotive force generated by said concentration detecting means.

5. The gas sensor according to claim 4, wherein said concentration-detecting means comprises:

said detecting electrode formed at the inside of a second chamber in said substrate for introducing said measurement gas after being pumping-processed by said main pumping means thereinto;

said reference electrode formed in a reference gas-introducing chamber in said substrate for introducing a reference gas thereinto;

a solid electrolyte layer being interposed between said detecting electrode and said reference electrode.

6. The gas sensor according to claim 1, wherein said electrode in said second chamber in addition to said electric signal-generating conversion means, which is subjected to detection of said impedance by said impedance-detection means, is an electrode other than said detecting electrode.

7. The gas sensor according to claim 1, further comprising:

a concentration-measuring means for generating an electromotive force corresponding to a difference between an amount of said first predetermined gas component contained in said measurement gas during said pumping process performed by said main pumping means and an amount of said first predetermined gas component contained in a reference gas existing on a side of said reference electrode; and a main pumping control means for adjusting a level of said control voltage applied between said inner pumping electrode and said outer pumping electrode, on the basis of a magnitude of said electromotive force.

8. The gas sensor according to claim 7, wherein said electromotive force generated by said concentration measuring means is a terminal voltage generated at least between said reference electrode and a measuring electrode located in the vicinity of said main pumping means.

9. The gas sensor according to claim 7, wherein said electromotive force generated by said concentration-measuring means is a terminal voltage generated at least between said reference electrode and said inner pumping electrode of said main pumping means.

10. The gas sensor according to claim 1, wherein said impedance-detecting means comprises:

a signal-detecting circuit for detecting a voltage signal at a level corresponding to said impedance between said electrodes generated between said electrodes by supplying said alternating current between said electrodes subjected to said detection; and said heater control means comprises:

a comparator circuit for comparing a reference level with a level of a voltage signal supplied from a signal detecting circuit of said impedance-detecting means; and a switching circuit for performing ON/OFF control over electric power application to said heater on the basis of a comparison performed by said comparator circuit.

11. The gas sensor according to claim 10, wherein said signal-detecting circuit comprises a filter circuit for converting an alternating current signal generated between said electrodes into said voltage signal at said level corresponding to said impedance between said electrodes.

12. The gas sensor according to claim 10, wherein:

said alternating current-generating circuit is wired and connected such that said alternating current is supplied not only between said electrodes but also to a resistor designed to have a resistance value corresponding to a normal impedance between said electrodes, and wherein said signal-detecting circuit comprises:

a first detection circuit for converting an alternating current generated between said electrodes into a voltage signal at said level corresponding to said impedance between said electrodes;

a second detection circuit for converting an alternating current signal generated in said resistor into a voltage signal at a level corresponding to an impedance of said resistor, to be used as a reference signal; and a differential circuit for determining a difference between said voltage signal outputted from said first detection circuit and said reference signal outputted from said second detection circuit, and outputting said difference as a deviation signal.

13. The gas sensor according to claim 1, wherein said impedance-detecting means detects said impedance between any one of said electrodes of said main pumping means and said reference electrode.

14. The gas sensor according to claim 1, further comprising an auxiliary pumping means including an auxiliary pumping electrode located in the vicinity of said detecting electrode, for pumping-processing said first predetermined gas component contained in said measurement gas after being pumping processed by said main pumping means, on the basis of a voltage applied between said auxiliary pumping electrode and said reference electrode.

15. The gas sensor according to claim 14, wherein said impedance-detecting means detects an impedance between said auxiliary electrode and any one of said electrodes of said main pumping means.

16. The gas sensor according to claim 1, wherein said main pumping means comprises:

said inner pumping electrode and said outer pumping electrode located at the inside and outside of a first chamber in said substrate for introducing said measurement gas therein;

a solid electrolyte layer being interposed between said both electrodes.

17. The gas sensor according to claim 16, further comprising:

a first diffusion rate-determining section provided at a passage to introduce said measurement gas from said external space into said first chamber, for giving a predetermined diffusion resistance to said measurement gas; and a second diffusion rate-determining section provided at a passage to introduce said measurement gas after being pumping-processed by said main pumping means into said second chamber, for giving a predetermined diffusion resistance to said measurement gas.

18. The gas sensor according to claim 17, further comprising a third diffusion rate-determining section provided at a passage for said measurement gas to enter said detecting electrode in said second chamber, for giving a predetermined diffusion resistance to said measurement gas.

* * * * *